(12) United States Patent
Yamada et al.

(10) Patent No.: US 10,231,920 B2
(45) Date of Patent: Mar. 19, 2019

(54) SKIN CLEANSING COMPOSITION

(71) Applicant: KAO CORPORATION, Tokyo (JP)

(72) Inventors: Kouhei Yamada, Sumida-ku (JP); Hitoshi Tajima, Chiba (JP)

(73) Assignee: KAO CORPORATION, Tokyo (JP)

( * ) Notice: Subject to any disclaimer, the term of this patent is extended or adjusted under 35 U.S.C. 154(b) by 120 days.

(21) Appl. No.: 15/322,245

(22) PCT Filed: Jun. 29, 2015

(86) PCT No.: PCT/JP2015/068675
§ 371 (c)(1),
(2) Date: Dec. 27, 2016

(87) PCT Pub. No.: WO2016/002713
PCT Pub. Date: Jan. 7, 2016

(65) Prior Publication Data
US 2017/0151159 A1    Jun. 1, 2017

(30) Foreign Application Priority Data

Jun. 30, 2014 (JP) ................. 2014-135422
Jun. 30, 2014 (JP) ................. 2014-135423

(51) Int. Cl.
| | |
|---|---|
| *A61K 8/37* | (2006.01) |
| *A61K 8/39* | (2006.01) |
| *A61K 8/60* | (2006.01) |
| *A61K 8/86* | (2006.01) |
| *A61K 8/92* | (2006.01) |
| *C11D 1/66* | (2006.01) |
| *C11D 1/72* | (2006.01) |
| *C11D 3/20* | (2006.01) |
| *C11D 3/22* | (2006.01) |
| *A61Q 1/14* | (2006.01) |
| *C11D 1/825* | (2006.01) |
| *A61Q 19/10* | (2006.01) |
| *C11D 3/37* | (2006.01) |
| *C11D 1/74* | (2006.01) |

(52) U.S. Cl.
CPC ............. *A61K 8/86* (2013.01); *A61K 8/37* (2013.01); *A61K 8/375* (2013.01); *A61K 8/39* (2013.01); *A61K 8/602* (2013.01); *A61K 8/604* (2013.01); *A61K 8/92* (2013.01); *A61Q 1/14* (2013.01); *A61Q 19/10* (2013.01); *C11D 1/825* (2013.01); *C11D 3/2068* (2013.01); *C11D 3/2093* (2013.01); *C11D 3/3707* (2013.01); *C11D 1/662* (2013.01); *C11D 1/667* (2013.01); *C11D 1/72* (2013.01); *C11D 1/74* (2013.01)

(58) Field of Classification Search
CPC ... A61K 8/37; A61K 8/39; A61K 8/60; A61K 8/86; A61K 8/92; C11D 1/66; C11D 1/662; C11D 1/72; C11D 3/20; C11D 3/2065; C11D 3/22; A61Q 1/14
See application file for complete search history.

(56) References Cited

U.S. PATENT DOCUMENTS

| | | |
|---|---|---|
| 2004/0136943 A1 | 7/2004 | Tomokuni |
| 2006/0078525 A1 | 4/2006 | Tomokuni |
| 2008/0182771 A1 | 7/2008 | Murase et al. |
| 2008/0188395 A1 | 8/2008 | Murase et al. |
| 2014/0142016 A1 | 5/2014 | Tomokuni et al. |

FOREIGN PATENT DOCUMENTS

| | | | |
|---|---|---|---|
| JP | 6-219923 A | 8/1994 | |
| JP | 7-285843 A | 10/1995 | |
| JP | 2004-217640 A | 8/2004 | |
| JP | 2006-117643 A | 5/2006 | |
| JP | 2006-232717 A | 9/2006 | |
| JP | 2006-306780 A | 11/2006 | |
| JP | 2008-184413 A | 8/2008 | |
| JP | 2008-184414 A | 8/2008 | |
| JP | 2008-184415 A | 8/2008 | |
| JP | 2010-280597 A | 12/2010 | |
| JP | 2011-126809 | * 6/2011 | ............... A61K 8/81 |
| JP | 2011-126809 A | 6/2011 | |
| JP | 2013-32348 A | 2/2013 | |

OTHER PUBLICATIONS

International Search Report dated Sep. 15, 2015, in PCT/JP2015/068675, filed Jun. 29, 2015.

* cited by examiner

*Primary Examiner* — Brian P Mruk
(74) *Attorney, Agent, or Firm* — Oblon, McClelland, Maier & Neustadt, L.L.P.

(57) ABSTRACT

A skin cleansing composition comprising the following components (A), (B), (C), (D), (E), (F), and (G):

(A) from 0.5 to 20% by mass of an oil agent having a viscosity at 30° C. of more than 30 mPa·s, (B) from 0.5 to 20% by mass of an oil agent having a viscosity at 30° C. of 30 mPa·s or less, (C) from 1 to 15% by mass of a nonionic surfactant having an HLB of 10 or more and having a residue obtained by removing a hydrogen atom from at least one hydroxyl group in sugar, reducing sugar, or polyglycerin as a hydrophilic group, (D) from 1 to 15% by mass of a nonionic surfactant having an HLB of 8 or less, (E) from 10 to 60% by mass of a polyhydric alcohol, (F) from 10 to 50% by mass of water, and (G) from 4 to 45% by mass of a nonionic surfactant having an HLB of 10 or more and having a polyoxyethylene chain as a hydrophilic group, wherein the mass ratio of the component (A) to the components (B), (A)/(B), is from 0.05 to 30, and the ratio of the total mass of the components (A) and (B) to the total mass of the components (C), (D), and (G), ((A)+(B))/((C)+(D)+(G)), is from 0.1 to 1.5.

17 Claims, No Drawings

SKIN CLEANSING COMPOSITION

FIELD OF THE INVENTION

The present invention relates to a skin cleansing composition.

BACKGROUND OF THE INVENTION

Recently, among women who make up, persistency of makeup has been increasingly required, and the usage rate of makeup-persistent makeup cosmetics such as foundations difficult to deteriorate due to sweat and sebum and waterproof mascaras is increasing. These makeup cosmetics, due to their performance, are difficult to remove with an aqueous makeup remover. For complete removal, use of a highly-detergent oil-based makeup remover is required. Oil-based makeup removers, which have a high oil content, enable a makeup-persistent makeup cosmetic to lift off the skin when blended with the makeup cosmetic, but the oil content contained in the makeup cosmetic or the makeup remover may not be sufficiently washed off with water.

To solve these problems, a makeup remover exhibiting a bicontinuous structure (Patent Literature 1) and a makeup remover exhibiting a microemulsion structure (Patent Literature 2) have been developed.

Additionally, makeup cosmetics such as foundations difficult to deteriorate due to sweat and sebum and waterproof mascaras, due to their performance, may be difficult to remove with a makeup remover, depending on the ways of use. Thus, to use a makeup remover, it has been necessary to extend the remover well and allow it to be sufficiently blended. However, when a makeup remover is blended with a makeup cosmetic, the remover can be lightly extended at first, whereas the remover may become gradually difficult to extend.

Consequently, excessive force may be required to extend the remover, a load may be applied on the face due to the force, and so on, and thus, the remover may not be blended sufficiently with the makeup cosmetic.

Accordingly, makeup removers having improved extension have been contemplated. For example, Patent Literature 3 discloses a liquid makeup remover exhibiting a microemulsion structure, Patent Literature 4 discloses a makeup remover in which a specific diglycerin derivative is used, Patent Literature 5 discloses a makeup remover in which a specific glycerin derivative is used, and so on.

CITATION LIST

Patent Literature

Patent Literature 1 JP-A-2004-217640
Patent Literature 2 JP-A-2006-117643
Patent Literature 3 JP-A-2004-217640
Patent Literature 4 JP-A-H7-285843
Patent Literature 5 JP-A-2006-232717

SUMMARY OF THE INVENTION

A first embodiment according to the present invention relates to a skin cleansing composition comprising the following components (A), (B), (C), (D), (E), and (F):

(A) from 0.5 to 20% by mass of an oil agent having a viscosity at 30° C. of more than 30 mPa·s, (B) from 0.5 to 20% by mass of an oil agent having a viscosity at 30° C. of 30 mPa·s or less, (C) from 1 to 15% by mass of a nonionic surfactant having an HLB of 10 or more and having a residue obtained by removing a hydrogen atom from at least one hydroxyl group in sugar, reducing sugar, or polyglycerin as a hydrophilic group.

(D) from 1 to 15% by mass of a nonionic surfactant having an HLB of 8 or less, (E) from 10 to 60% by mass of a polyhydric alcohol, and (F) from 10 to 50% by mass of water, where the mass ratio of the component (A) to the component (B), (A)/(B), is from 0.05 to 30.

A second embodiment according to the present invention relates to a skin cleansing composition comprising the following components (H), (I), (J), and (K):

(H) from 0.05 to 10% by mass of one or more glycerin derivatives selected from the group consisting of (h1) and (h2):

(h1) the formula (1)

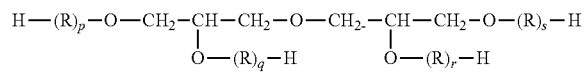

(1)

where R represents —[CH$_2$CH(CH$_3$)O]—, p, q, r, and s each represent an integer of from 0 to 20, and p+q+r+s represents an integer of from 4 to 20, (h2) the formula (2)

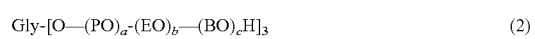

(2)

where Gly represents a residue obtained by removing a hydroxyl group from glycerin, PO represents an oxypropylene group, EO represents an oxyethylene group, a and b are the average addition mole number of each PO and EO and represent a value of from 1 to 50, the mass ratio of PD to EO, PO/EO, is from 1/5 to 5/1, BO represents an oxyalkylene group having 4 carbon atoms, and c is the average addition mole number of BO and represents a value of from 1 to 5, (I) from 3 to 35% by mass of an oil agent which is liquid at 30° C., (J) from 5 to 50% by mass of a nonionic surfactant selected from the group consisting of (j1), (j2), and (j3) and comprises at least (j1) and (j2), (j1) a nonionic surfactant having an HLB of 10 or more and having a residue obtained by removing a hydrogen atom from at least one hydroxyl group in sugar, reducing sugar, or polyglycerin as a hydrophilic group, (j2) a nonionic surfactant having an HLB of 8 or less, and (j3) a nonionic surfactant having an HLB of 10 or more and having a polyoxyethylene chain as a hydrophilic group, and (K) from 10 to 50% by mass of water, where the mass ratio of the components (H) to the components (J), (H)/(J), is from 0.001 to 0.5.

DETAILED DESCRIPTION OF THE INVENTION

First Embodiment

Regarding the problem of insufficient washing-off of the oil content contained in a makeup cosmetic or a makeup remover, conventional makeup removers of Patent Literatures 1, 2 and the like can allow the makeup cosmetic to lift off the skin, but fail to sufficiently wash the oil content contained in the makeup cosmetic or the makeup remover off. Thus, the skin after washing-off lacked a fresh feeling. Furthermore, after the makeup remover is washed off, the face may be further washed with a face wash to freshen the face. With a conventional makeup remover, the oil content which has not been completely washed off may be left on the skin, and the foam of the whipped face wash decreases while applied to the skin, and the foamability becomes reduced. Thus, it has not been able to sufficiently freshen the skin.

Accordingly, a makeup remover has been required which allows an oil content to be sufficiently removed from the skin by washing-off after the makeup remover is used and does not impair the foamability of a face wash when the face wash is subsequently used, providing a fresh skin feel.

The present inventors have found that a skin cleansing composition can be obtained by combining two oil agents each having a specific viscosity, specific two nonionic surfactants, a polyhydric alcohol, and water in a specific content, and that the skin cleansing composition allows the makeup remover to sufficiently remove an oil content from the skin by washing-off after the makeup remover is used and does not impair the foamability of a face wash when the face wash is subsequently used, providing a fresh skin feel.

The skin cleansing composition of the present invention has excellent detergency, enables an oil content to be sufficiently removed from the skin by washing-off after the makeup remover is used, and provides a fresh skin feel without impairing the foamability of a face wash when the face wash is subsequently used. The composition also has excellent rinsability.

A component (A) an oil agent used in the present invention has a viscosity at 30° C. of more than 30 mPa·s. The component (A) oil agent used in the present invention has a viscosity at 30° C. of preferably 40 mPa·s or more, more preferably 50 mPa·s or more, even more preferably 80 mPa·s or more, preferably 20,000 mPa·s or less, more preferably 10,000 mPa·s or less, even more preferably 1,000 mPa·s or less, further more preferably 200 mPa·s or less, in respect of improving detergency, rinsability, and stability in combination with a component (B) described below. The component (A) oil agent preferably has a viscosity at 30° C. of more than 30 mPa·s and 20,000 mPa·s or less, more preferably from 40 to 10,000 mPa·s, even more preferably from 50 to 1,000 mPa·s, further more preferably from 80 to 200 mPa·s.

Incidentally, the viscosity of the oil agent in the present invention is measured using a B-type viscometer (TV-B type, manufactured by Tokyo Keiki Inc.) with the rotor No. 1 at the number of revolutions of 60 rpm for a viscosity less than 100 mPa·s, with the rotor No. 1 at the number of revolutions of 12 rpm for a viscosity of 100 mPa·s or more and less than 500 mPa·s, with the rotor No. 1 at the number of revolutions of 6 rpm for a viscosity of 500 mPa·s or more and less than 1,000 mPa·s, with the rotor No. 3 at the number of revolutions of 12 rpm for a viscosity of 1,000 mPa·s or more and less than 10,000 mPa·s, and with the rotor No. 4 at the number of revolutions of 12 rpm for a viscosity of 10,000 mPa·s or more.

The component (A) oil agent used in the present invention preferably has an average molecular weight of from 350 to 950, more preferably from 375 to 700, even more preferably from 400 to 600, in respect of improving rinsability, detergency, and stability in combination with the component (B) described below.

As the component (A) oil agent, liquid oils usually used in cosmetics can be used. Examples thereof include hydrocarbon oils such as liquid paraffin and hydrogenated polybutene having a viscosity at 30° C. of more than 30 mPa·s, ester oils, ether oils, silicone oils, and animal and plant oils. Of these, hydrocarbon oils such as liquid paraffin and hydrogenated polybutene having a viscosity at 30° C. of more than 30 mPa·s are preferable, from the viewpoint of improving the detergency, rinsability, stability, and foam retention on washing the face after makeup is removed in combination with the component (B) described below.

Also as the component (A) oil agent, commercially available products, for example, HICALL K-350 (115 mPa·s, manufactured by KANEDA Co., Ltd.) as liquid paraffin and PARLEAM 18 (18,160 mPa·s, manufactured by NOR CORPORATION) and PARLEAM 6 (33 mPa·s, manufactured by NOF CORPORATION) as hydrogenated polybutene can be used.

One or more components (A) can be used. The content is 0.5% by mass or more, preferably 2% by mass or more, even more preferably 3.5% by mass or more, 20% by mass or less, preferably 14% by mass or less, even more preferably 10% by mass or less in the whole composition, in respect of improving detergency, stability, and rinsability. Moreover, the content of the component (A) is from 0.5 to 20% by mass, preferably from 2 to 14% by mass, more preferably from 3.5 to 10% by mass in the whole composition.

The content of the component (A) is preferably 1% by mass or more and preferably 18.6% by mass or less in the whole composition.

The component (B) oil agent used in the present invention has a viscosity at 30° C. of 30 mPa·s or less. The component (B) oil agent used in the present invention preferably has a viscosity at 30° C. of 2 mPa·s or more, more preferably 3 mPa·s or more, even more preferably 4 mPa·s or more, preferably 25 mPa·s or less, more preferably 20 mPa·s or less, even more preferably 15 mPa·s or less, in respect of improving rinsability, detergency, and stability in combination with the component (A). The component (B) oil agent preferably has a viscosity at 30° C. of from 2 to 25 mPa·s, more preferably from 3 to 20 mPa·s, even more preferably from 4 to 15 mPa·s.

The component (B) oil agent preferably has a viscosity at 30° C. of 27 mPa·s or less.

The component (B) oil agent used in the present invention has an average molecular weight of preferably 330 or less, more preferably from 100 to 315, even more preferably from 200 to 300, in respect of improving rinsability, detergency, and stability in combination with the component (A).

As such an oil agent, liquid oils usually used in cosmetics can be used. Examples thereof include hydrocarbon oils having a viscosity at 30° C. of 30 mPa·s or less such as light liquid isoparaffin and hydrogenated polybutene; monoester oils such as isopropyl palmitate, isopropyl myristate, octyldodecyl myristate, cetyl 2-ethylhexanoate, isononyl isononanoate, and isotridecyl isononanoate; diester oils such as neopentyl glycol dicaprate; triester oils such as tri(2-ethylhexanoate)glycerin and tri(caprylic/capric acid) glycerin; ether oils such as alkyl-1,3-dimethylbutyl ether and dicaprylyl ether; methylcyclopolysiloxanes such as decamethylcyclopentasiloxane and octamethylcyclotetrasiloxane, and methypolysiloxanes having a viscosity at 30° C. of 30 mPa·s or less.

Of these, hydrocarbon oils, monoester oils, diester oils, triester oils, ether oils, and methylcyclopolysiloxanes are preferable, hydrocarbon oil, monoester oils, and ether oils are more preferable, monoester oils and ether oils are even more preferable, and monoester oils are further more preferable, in respect of improving rinsability, detergency, and stability in combination with the component (A).

As the component (B), isononyl isononanoate, tri (caprylic/capric acid)glycerin, dicaprylyl ether, and decamethylcyclopentasiloxane are preferable, isononyl isononanoate and dicaprylyl ether are more preferable, and isononyl isononanoate is even more preferable.

As the component (B) oil agent, commercially available products, for example, MARUKASOL R (5 mPa·s, manufactured by Maruzen Petrochemical Co., Ltd.), IP solvents 1620 and 2028 (both manufactured by Idemitsu Petrochemical Co., Ltd.), Isopar L and Isopar H (both manufactured by Exxon Mobil Chemical Company), and Isosol 300 and Isosol 400 (both manufactured by Shin-Nippon Petrochemical Co., Ltd.) as light liquid isoparaffin; PARLEAM 4 (5 mPa·s, manufactured by NOF Corporation) and PARLEAM EX (17 mPa·s, manufactured by NOF Corporation) as hydrogenated polybutene; Cetiol OE (5 mPa·s, manufactured by BASF) as dicaprylyl ether; ASE166K (8 mPa·s, manufactured by Kao Corporation) as 1,3-dimethylbuthyl ether; SALACOS 99 (7.4 mPa·s, manufactured by Nisshin Oil Mills, Ltd.) as isononyl isononanoate; EXEPARL IPM (10 mPa·s, manufactured by Kao Corporation) as isopropyl myristate; EXEPARL IPP (10 mPa·s, manufactured by Kao Corporation) as isopropyl palmitate; COCONARD MT (27 mPa·s, manufactured by Kao Corporation) as tri(caprylic/capric acid) glyceryl; and Silicone SH245 (3 mPa·s, manufactured by Dow Corning Toray Co., Ltd.) as octamethylcyclotetrasiloxane can be used.

One or more components (B) can be used. The content is 0.5% by mass or more, preferably 1.2% by mass or more, more preferably 2% by mass or more, 20% by mass or less, preferably 10% by mass or less, more preferably 8% by mass or less in the whole composition, in respect of improving rinsability, detergency, and stability. The content of the component (B) is from 0.5 to 20% by mass, preferably from 1.2 to 10% by mass, more preferably from 2 to 8% by mass.

The content of the component (B) is preferably 1% by mass or more, preferably 11.5% by mass or less in the whole composition.

In the present invention, the mass ratio of the component (A) to the component (B), (A)/(B), is preferably 0.05 or more, more preferably 0.25 more, even more preferably 0.5 or more, preferably 30 or less, more preferably 8 or less, even more preferably 5 or less, in respect of improving spreadability one minute after application, rinsability, detergency, foam retention on washing the face after makeup is removed, and retention of a moist feeling, and reducing a remaining feeling and further in respect that the skin cleansing composition takes an isotropic single liquid phase exhibiting a bicontinuous structure described below. The mass ratio of the component (A) to the component (B), (A)/(B), is from 0.05 to 30, preferably from 0.25 to 8, more preferably from 0.5 to 5.

The mass ratio of the component (A) to the component (B), (A)/(B), is preferably 0.1 or more, preferably 9 or less.

In the present invention, the total mass of the whole oil agents including the components (A) and (B) is preferably 3% by mass or more, more preferably 4% by mass or more, even more preferably 6% by mass or more, preferably 35% by mass or less, more preferably 24% by mass or less, even more preferably 18% by mass or less in the whole composition, in respect of improving spreadability one minute after application, rinsability, detergency, foam retention on washing the face after makeup is removed, and retention of a moist feeling, and reducing a remaining feeling and further in respect that the skin cleansing composition takes an isotropic single liquid phase exhibiting a bicontinuous structure described below. The total mass of the whole oil agents including the components (A) and (B) is preferably from to 35% by mass, more preferably from 4 to 24% by mass, even more preferably from 6 to 18% by mass in the whole composition.

The component (C) nonionic surfactant used in the present invention has a residue obtained by removing a hydrogen atom from at least one hydroxyl group in sugar, reducing sugar, or polyglycerin as a hydrophilic group, and examples thereof include polyglycerin fatty acid esters, polyglycerin alkyl ethers, sucrose fatty acid esters, and alkyl polyglucosides.

As the polyglycerin fatty acid ester, esters of polyglycerin and a fatty acid having from 8 to 22 carbon atoms are preferable in respect of improving rinsability, detergency, and stability, and examples thereof include polyglycerin octanoate ester, polyglycerin 2-ethylhexanoate ester, polyglycerin decanoate ester, polyglycerin laurate ester, polyglycerin myristate ester, polyglycerin palmitate ester, polyglycerin isostearate ester, polyglycerin stearate ester, polyglycerin oleate ester, and polyglycerin behenate ester. Of these, monoesters of a polyglycerin having a degree of polymerization of from 3 to 15 and a fatty acid having from 12 to 18 carbon atoms are preferable, monoesters of a polyglycerin having a degree of polymerization of from 8 to 12 and a fatty acid having from 12 to 18 carbon atoms are more preferable, and monoesters of polyglycerin having a degree of polymerization of from 8 to 12 and a fatty acid having from 12 to 14 carbon atoms are even more preferable.

As the polyglycerin alkyl ether, ethers of a polyglycerin and an alkyl group having from 8 to 22 carbon atoms are preferable in respect of improving rinsability, detergency, and stability, examples thereof include polyglycerin octyl ether, polyglycerin decyl ether, polyglycerin lauryl ether, polyglycerin myristyl ether, polyglycerin palmityl ether, polyglycerin isostearyl ether, polyglycerin stearyl ether, polyglycerin oleyl ether, and polyglycerin behenyl ether. Of these, monoethers of a polyglycerin having a degree of polymerization of from 3 to 15 and an alkyl group having from 12 to 18 carbon atoms are preferable, monoethers of a polyglycerin having a degree of polymerization of from 8 to 12 and a fatty acid having from 12 to 18 carbon atoms are more preferable, and monoethers of polyglycerin having a degree of polymerization of from 8 to 12 and a fatty acid having from 12 to 14 carbon atoms are even more preferable.

As the sucrose fatty acid ester, esters of a fatty acid having from 8 to 22 carbon atoms and sucrose are preferable in respect of improving rinsability, detergency, and stability, and examples thereof include sucrose octanoate ester, sucrose 2-ethylhexanoate ester, sucrose decanoate ester, sucrose laurate ester, sucrose myristate ester, sucrose palmitate ester, sucrose isostearate ester, sucrose stearate ester, sucrose oleate ester, and sucrose behenate ester. Of these, monoesters of fatty acid having from 12 to 18 carbon atoms and sucrose are more preferable, and sucrose laurate ester and sucrose stearate ester are even more preferable.

As the alkyl polyglucoside, those having an alkyl group having from 8 to 22 carbon atoms and have a degree of condensation of glucoside units of from 1 to 7 are preferable, in respect of improving rinsability, detergency, and stability, and examples thereof include octyl polyglucoside, 2-ethylhexyl polyglucoside, decyl polyglucoside, lauryl polyglucoside, myristyl polyglucoside, palmityl polyglucoside, isostearyl polyglucoside, stearyl lauryl polyglucoside, oleyl polyglucoside, and behenyl polyglucoside. Of these, as the alkyl polyglucoside, those having an alkyl group having from 8 to 11 carbon atoms and have a degree of condensation of glucoside units of from 1 to 1.4 and those having an alkyl group having from 12 to 14 carbon atoms and have a degree of condensation of glucoside units of from 1.5 to 4.0 are more preferable, and decyl polyglucoside is even more preferable.

As the component (C), commercially available products such as Sunsoft Q-12S (HLB: 15.5, manufactured by Taiyo Kagaku Co., Ltd.) and Sunsoft M-12J (HLB: 15.5, manufactured by Taiyo Kagaku Co., Ltd.) as polyglycerin (10) monolaurate ester, Sunsoft Q-14S (HLB: 14.5, manufactured by Taiyo Kagaku Co., Ltd.) as polyglycerin (10) monomyristate ester, and MYDOL 10 (HLB! 17, active ingredient content 40% by mass, manufactured by Kao Corporation) as decyl polyglucoside can be used.

As the component (C) nonionic surfactant, those having a residue obtained by removing a hydrogen atom from at least one hydroxyl group in sugar are preferable in respect of improving rinsability, detergency, and stability and further in respect that the skin cleansing composition takes an isotropic single liquid phase exhibiting a bicontinuous structure described below, alkyl polyglucosides are more preferable, and decyl polyglucoside is even more preferable.

The component (C) nonionic surfactant has an HLB of 10 or more, and the HLB is preferably from 10 to 20, more preferably from 12 to 19, even more preferably from 14 to 18, in respect of improving rinsability, detergency, and stability and further in respect that the skin cleansing composition takes an isotropic single liquid phase exhibiting a bicontinuous structure described below.

The HLB (Hydrophilic-Lipophilic Balance) herein indicates the molecular weight of the hydrophilic group moiety relative to the total molecular weight of the surfactant, and the HLB for polyoxyethylenic nonionic surfactants can be determined according to Griffin's formula shown below:

HLB value=$E/5$

E: % by mass of the polyoxyethylene moiety contained in the surfactant molecule

One or more components (C) can be used. The content is 1% by mass or more, preferably 1.25% by mass or more, more preferably 1.5% by mass or more, 15% by mass or less, preferably 8% by mass or less, even more preferably 6% by mass or less, further more preferably 4.5% by mass or less in the whole composition, in respect of improving rinsability, detergency, and stability and further in respect that the skin cleansing composition takes an isotropic single liquid phase exhibiting a bicontinuous structure described below. The content of the component (C) is from 1 to 15% by mass, preferably from 1 to 8% by mass, more preferably from 1.25 to 6% by mass, even more preferably from 1.5 to 4.5% by mass in the whole composition.

The content of the component (C) is preferably 1.1% by mass or more, more preferably 6.3% by mass or less in the whole composition.

The component (D) nonionic surfactant used in the present invention has an HLB of 8 or less, and the HLB is preferably from 3 to 8, more preferably from 4 to 8, even more preferably from 5 to 8 in respect of improving rinsability, detergency, and stability and further in respect that the skin cleansing composition takes an isotropic single liquid phase exhibiting a bicontinuous structure described below.

Specific examples thereof include monoglycerin monofatty acid esters such as monoglyceryl monoisostearate; polyglycerin monofatty acid esters such as diglyceryl monooleate and diglyceryl monoisostearate; polyglycerin monoalkyl ethers such as 2-ethylhexyl diglyceryl ether, monoglycerin monoalkyl ethers such as monoisostearyl glyceryl ether; and polyoxyethylene monofatty acid esters such as polyoxyethylene (5) monostearate ester.

As the component (D), those having a glycerin structure are preferable, in respect of improving rinsability, detergency, and stability and further in respect that the skin cleansing composition takes an isotropic single liquid phase exhibiting a bicontinuous structure described below. Monoglycerin monofatty acid esters, polyglycerin monofatty acid esters, and monoglycerin monoalkyl ethers are preferable, polyglycerin monofatty acid esters and monoglycerin monoalkyl ethers are more preferable, and polyglycerin monofatty acid esters are preferable.

Also, diglyceryl monooleate, diglyceryl monoisostearate, and monoisostearyl glyceryl ether are preferable, and diglyceryl monoisostearate is more preferable.

Also as the component (D), PENETOL GE-IS (HLB: 5, manufactured by Kao Corporation) as monoisostearyl glyceryl ether, POEM DO-100V (HLB: 7, manufactured by RIKEN VITAMIN Co., Ltd.) as diglyceryl monooleate, Cosmol 41V (HLB: 8, manufactured by The Nisshin OilliO Group, Ltd.) as diglyceryl monoisostearate, and the like can be used.

One or more components (D) can be used. The content is 1% by mass or more, preferably 2% by mass or more, more preferably 2.8% by mass or more, even more preferably 3% by mass or more, 15% by mass or less, preferably 12% by mass or less, more preferably 9% by mass or less, even more preferably 6% by mass or less in the whole composition, in respect of improving rinsability, detergency, and stability and further in respect that the skin cleansing composition takes an isotropic single liquid phase exhibiting a bicontinuous structure described below. The content is from 1 to 15% by mass, preferably from 2 to 12% by mass, more preferably from 2.8 to 9% by mass, even more preferably from 3 to 6% by mass in the whole composition.

The content of the component (D) is preferably 2.7% by mass or more, preferably 9.7% by mass or less in the whole composition.

In the present invention, the mass ratio of the component (A) to the component (D), (A)/(D), is preferably 0.1 or more, more preferably 0.5 or more, even more preferably 0.7 or more, preferably 2.1 or less, more preferably 2.0 or less, even more preferably 1.9 or less, in respect of improving spreadability one minute after application, rinsability, detergency, foam retention on washing the face after makeup is removed, and retention of a moist feeling, and reducing the remaining feeling and further in respect that the skin cleansing composition takes an isotropic single liquid phase exhibiting a bicontinuoils structure described below. The mass ratio of the component (A) to the component (D), (A)/(D), is preferably from 0.1 to 2.1, more preferably from 0.5 to 2.0, even more preferably from 0.7 to 1.9.

The mass ratio of the component (A) to the component (D), (A)/(D), is preferably 0.2 or more, preferably 2.3 or less.

The component (E) polyhydric alcohol is those used in common skin cleansing compositions, and examples thereof include 1,3-butylene glycol, propylene glycol, glycerin; sorbitol, diglycerin, dipropylene glycol, 1,3-propanediol, polyoxyethylene methyl glucoside, polyethylene glycols having an average molecular weight of 2,000 or less, glycerin derivatives represented by the formula (1), and glycerin derivatives represented by the formula (2).

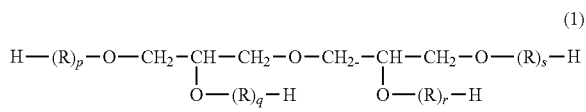

$$H-(R)_p-O-CH_2-CH-CH_2-O-CH_2-CH-CH_2-O-(R)_s-H \quad (1)$$
$$\phantom{H-(R)_p-O-CH_2-}|\phantom{CH-CH_2-O-CH_2}|$$
$$\phantom{H-(R)_p-O-CH_2}O-(R)_q-H\phantom{xx}O-(R)_r-H$$

where R represents —[CH$_2$CH(CH$_3$)O]—, p, q, r, and s each represent an integer of from 0 to 20, and p+q+r+s represents an integer of from 4 to 20, and

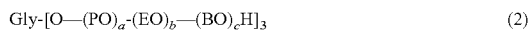

$$Gly-[O-(PO)_a-(EO)_b-(BO)_cH]_3 \quad (2)$$

where Gly represents a residue obtained by removing hydroxyl groups from glycerin, PO represents an oxypropylene group, EO represents an oxyethylene group, a and b are the average addition mole number of each PO and EO and represent a value of from 1 to 50, the mass ratio of PO to EO, PO/EO, is from 1/5 to 5/1, BO represents an oxyalkylene group having 4 carbon atoms, and c is the average addition mole number of BO and represents a value of from 1 to 5.

Of these, 1,3-butylene glycol, glycerin, sorbitol, glycerin derivatives represented by the formula (1), and glycerin derivatives represented by the formula (2) are preferable, and 1,3-butylene glycol, glycerin and glycerin derivatives represented by the formula (1) are more preferable, in respect of improving rinsability, detergency, stability, and retention of a moist feeling.

Preferable glycerin derivatives represented by the formula (1) are specifically polyoxypropylene (9) diglyceryl ether having an n of 9 and polyoxypropylene (14) diglyceryl ether having an n of 14.

Specific examples of the glycerin derivatives represented by the formula (2) include those having an average addition mole number of (EO) of 8, an average addition mole number of (PO) of 5, and the average addition mole number of (BO) of 3. Polyoxybutylene polyoxyethylene polyoxypropylene glyceryl ether (3BO) (8EO) (5PO) is preferable.

As the component (E), 1,3-butylene glycol, glycerin, sorbitol and the like which can be used are general-purpose products. Commercially available products, such as SY-DP9 (manufactured by SAKAMOTO YAKUHIN KOGYO CO., LTD.) as polyoxypropylene (9) diglyceryl ether, SY-DP14 (manufactured by SAKAMOTO YAKUHIN KOGYO CO., LTD.) as polyoxypropylene (14) diglyceryl ether, and WILBRIDE S-753 (manufactured by NOF CORPORATION) as polyoxybutylene polyoxyethylene polyoxypropylene glyceryl ether (330) (8EO) (5PO) can be used.

One or more components (E) can be used. The content is 10% by mass or more, preferably 17% by mass or more, more preferably 20% by mass or more, even more preferably 30% by mass or more, 60% by mass or less, preferably 48% by mass or less, more preferably 47% by mass or less, even more preferably 46% by mass or less in the whole composition, in respect of improving rinsability, detergency, stability, and retention of a moist feeling. The content of the component (E) is from 10 to 60% by mass, preferably from 17 to 48% by mass, more preferably from 20 to 47% by mass, even more preferably from 30 to 46% by mass in the whole composition.

The content of the component (E) is preferably 16% by mass or more, preferably 50.3% by mass or less in the whole composition.

The content of the component (F) water is from 10 to 50% by mass, preferably from 17 to 45% by mass, more preferably from 18 to 35% by mass in the whole composition, in respect of improving rinsability, detergency, stability, and usability and further in respect that the skin cleansing composition takes an isotropic single liquid phase exhibiting a bicontinuous structure described below.

The skin cleansing composition of the present invention can further contain (G) a nonionic surfactant having an HLB of 10 or more and having a polyoxyethylene chain as a hydrophilic group (except the component (C)) to thereby enable rinsability, detergency, and stability to be improved. The component (G) has an HLB of preferably from 10 to 20, more preferably from 10 to 17, even more preferably from 10.5 to 15, in respect of improving rinsability, detergency, and stability and further in respect that the skin cleansing composition takes an isotropic single liquid phase exhibiting a bicontinuous structure described below.

Specific examples thereof include polyoxyethylene monofatty acid esters such as polyoxyethylene (12) monolaurate ester, tetrafatty acid polyoxyethylene sorbit such as tetraoleic acid polyoxyethylene (30) sorbit, polyoxyethylene glycerin fatty acid esters such as polyoxyethylene (7) coconut oil fatty acid glycerin, polyoxyethylene alkyl ethers such as polyoxyethylene (20) octyldodecyl ether, polyoxyethylene alkylphenyl ethers such as polyoxyethylene (20) nonylphenyl ether, polyoxyethylene castor oil derivatives such as polyoxyethylene (50) castor oil, polyoxyethylene cured castor oil derivatives such as polyoxyethylene (60) cured castor oil monoisolaurate, and polyoxyethylene sorbitan fatty acid esters such as polyoxyethylene (20) sorbitan monostearate ester and polyoxyethylene (30) sorbitan tristearate ester. Additionally, of these, those having 8 or more carbon atoms in the hydrophobic group are preferable, and those having 12 or more carbon atoms in the hydrophobic group are more preferable, in respect of improving rinsability.

As the component (G), polyoxyethylene monofatty acid esters, polyoxyethylene glycerin fatty acid esters, tetrafatty acid polyoxyethylene sorbit, and polyoxyethylene sorbitan fatty acid esters are preferable, polyoxyethylene monofatty acid esters, polyoxyethylene glycerin fatty acid esters, and tetrafatty acid polyoxyethylene sorbit are more preferable, polyoxyethylene (12) monolaurate ester, polyoxyethylene (7) coconut oil fatty acid glycerin, and tetraoleic acid polyoxyethylene (30) sorbit are even more preferable, and polyoxyethylene (12) monolaurate ester and tetraoleic acid polyoxyethylene (30) sorbit are further more preferable, in respect of improving stability, rinsability, and detergency and further in respect that the skin cleansing composition takes an isotropic single liquid phase exhibiting a bicontinuous structure described below.

As the component (G), commercially available products, such as EMANON 1112 (HLB: 13.7, manufactured by Kao Corporation) as polyoxyethylene (12) monolaurate ester; RHEODOL 430V (HLB: 10.5, manufactured by Kao Corporation) as tetraoleic acid polyoxyethylene (30) sorbit; LEVENOL C301 (HLB: 13, manufactured by Kao Corporation) as polyoxyethylene coconut oil fatty acid glycerin; and RHEODOL TW-O320V (HLB11, manufactured by Kao Corporation) as polyoxyethylene (20) sorbitan tristearate also can be used.

One or more components (G) can be used. The content is preferably 4% by mass or more, more preferably 5% by mass or more, even more preferably 9% by mass or more, preferably 45% by mass or less, more preferably 28% by mass or less, even more preferably 25% by mass or less in the whole composition, in respect of improving rinsability, detergency, and stability and further in respect that the skin cleansing composition takes an isotropic single liquid phase exhibiting a bicontinuous structure described below. The content is preferably from 4 to 45% by mass, more preferably from 5 to 28% by mass, even more preferably from 9 to 25% by mass in the whole composition.

The content of the component (G) is preferably 4.2% by mass or more, preferably 30.2% by mass or less in the whole composition.

In the present invention, the total mass of the components (C), (D), and (G) is preferably 7% by mass or more, more preferably 9% by mass or more, even more preferably 15% by mass or more, preferably 50% by mass or less, more preferably 40% by mass or less, even more preferably 30% by mass or less in the whole composition, in respect of improving spreadability one minute after application, rinsability, detergency, and foam retention on washing the face after makeup is removed and reducing a remaining feeling and in respect that the skin cleansing composition takes an isotropic single liquid phase exhibiting a bicontinuous structure described below. The total mass of the components (C), (D), and (G) is preferably from 7 to 50% by mass, more preferably from 9 to 40% by mass, even more preferably from 15 to 30% by mass in the whole composition.

The total mass of the components (C), (D), and (G) is preferably 8% by mass or more, preferably 46% by mass or less in the whole composition.

The skin cleansing composition of the present invention preferably contains the components (C), (D), and (G) in combination as a nonionic surfactant, in respect of exhibiting an isotropic single liquid phase exhibiting a bicontinuous structure described below. As the combination of the components (C), (D), and (G), in respect of improving rinsability, detergency, and stability, the combination of the component (C): an alkyl polyglucoside, the component (D): a monoglycerin monofatty acid ester, a polyglycerin monofatty acid ester, a monoglycerin monoalkyl ether, and the component (G): a polyoxyethylene monofatty acid ester, a tetrafatty acid polyoxyethylene sorbit is preferable, the combination of the component (C): an alkyl polyglucoside, the component (D): a polyglycerin monofatty acid ester, and the component (G): a polyoxyethylene monofatty acid ester, a tetrafatty acid polyoxyethylene sorbit is more preferable, and the combination of the component (C): decyl polyglucoside, the component (D): diglyceryl monoisostearate, and the component (G): polyoxyethylene (12) laurate ester, tetraoleic acid polyoxyethylene (30) sorbit is even more preferable.

Additionally, the ratio of the total mass of the components (A) and (B) to the total mass of the components (C), (D), and (G), ((A)+(B))/((C)+(D)+(G)), is preferably 0.1 or more, more preferably 0.21 or more, even more preferably 0.23 or more, further more preferably 0.25 or more, preferably 1.5 or less, more preferably 1.3 or less, even more preferably 1.2 or less, further more preferably 0.8 or less, in respect of improving spreadability one minute after application, rinsability, detergency, and foam retention on washing the face after makeup is removed and reducing a remaining feeling and further in respect that the skin cleansing composition takes an isotropic single liquid phase exhibiting a bicontinuous structure described below. The ratio of the total mass of the components (A) and (B) to the total mass of the components (C), (D), and (G), ((A)+(B))/((C)+(D)+(G)), is preferably from 0.1 to 1.5, more preferably from 0.21 to 1.3, even more preferably from 0.23 to 1.2, further more preferably from 0.25 to 0.8.

The ratio of the total mass of the components (A) and (B) to the total mass of the components (C), (D), and (G), ((A)+(B))/((C)+(D)+(G)), is preferably 0.22 or more, preferably 1.4 or less.

The skin cleansing composition of the present invention may further contain components usually used in cleansers, for example, a nonionic surfactant other than components (C), (D), and (G), oils and fats in the form of paste or wax at 30° C., a water-soluble thickener, an anionic surfactant, a cationic surfactant, an amphoteric surfactant, ethanol, a bactericide, a moisturizing agent other than the component (E), a colorant, a preservative, a texture improver, a fragrance, an anti-inflammatory agent, a whitening agent, an antiperspirant, an ultraviolet absorber, a water-soluble inorganic salt, and a water-soluble organic salt having from 1 to 8 carbon atoms.

One or more nonionic surfactants other than components (C), (D), and (G) can be used in combination. The content is preferably 5% by mass or less, more preferably 3% by mass or less, even more preferably 1% by mass or less, further more preferably 0.5% by mass or less, further more preferably substantially 0% by mass in the whole composition, in respect of improving rinsability, detergency, and stability.

One or more oils and fats in the form of paste or wax at 30° C. can be used in combination. The content is preferably 1% by mass or less, more preferably 0.5% by mass or less, even more preferably 0.1% by mass or less, further more preferably substantially 0% by mass in the whole composition, in respect of improving rinsability, detergency, and stability.

As the water-soluble thickener, one or more selected from the group consisting of acrylate polymers comprising, as the constituent unit, acrylic acid or methacrylic acid, polysaccharide such as pullulan, cellulosic polymer, and polyethylene glycols having a weight average molecular weight of 200,000 or more and 5,000,000 or less can be used in combination.

The acrylate polymers are those synthesized by using acrylic acid or methacrylic acid for example, as the monomer, and examples thereof include carboxyvinyl polymers and acrylic acid-alkyl methacrylate copolymers. Acrylic acid-alkyl methacrylate copolymers are preferable, and copolymers of acrylic acid and an alkyl methacrylate having from 10 to 30 carbon atoms ((acrylic acid/alkyl acrylate (C10-30)) copolymers) are more preferable. Examples of commercially available products include PEMULEN TR-1, PEMULEN TR-2, and Carbopol ETD2020 (manufactured by Lubrizol Advanced Materials).

Examples of the polysaccharide include pullulan and sodium hyaluronate. Examples of the cellulosic polymer include methyl cellulose, ethyl cellulose, hydroxyethyl cellulose, hydroxypropyl cellulose, hydroxypropyl methyl cellulose, and carboxymethyl cellulose sodium.

The weight average molecular weight of the polyethylene glycol as the thickener is preferably 200,000 or more, more preferably 300,000 or more, far more preferably 500,000 or more, even more preferably 1,000,000 or more, still even more preferably 2,000,000 or more, preferably 5,000,000 or less, more preferably 4,000,000 or less, even more preferably 3,500,000 or less. Examples of the commercially available product include ALKOX series (Meisel Chemical Works, Ltd., polyethylene glycol): ALKOX E30 (weight average molecular weight: from 300,000 to 500,000), ALKOX E-45 (weight average molecular weight: from 600,000 to 800,000), ALKOX E-60 (weight average molecular weight: from 1,000,000 to 1,200,000), ALKOX E-75 (weight average molecular weight: from 2,000,000 to 2,500,000), and ALKOX E-100 (weight average molecular weight: from 2,500,000 to 3,000,000).

One water-soluble thickener can be used alone or two or more can be used in combination. The content is preferably 0.5% by mass or less, more preferably 0.1% by mass or less, even more preferably less than 0.05% by mass, further more preferably 0.01% by mass or less, further more preferably substantially 0% by mass in the whole composition, in respect of improving rinsability, detergency, and usability.

One of anionic surfactant, cationic surfactant, and amphoteric surfactant can be used alone or two or more can be used in combination. The content is preferably 1% by mass or less, more preferably 0.5% by mass or less, even more preferably 0.1% by mass or less, further more preferably substantially 0% by mass in the whole composition, in respect of improving rinsability, detergency, and stability.

In order to spread the skin cleansing composition evenly, the content of ethanol is preferably 5% by mass or less, more preferably 3% by mass or less, far more preferably 1% by mass or less, even more preferably 0.5% by mass or less, still even more preferably substantially 0% by mass in the whole composition.

One preservative can be used alone or two or more can be used in combination. Examples of an oil-based preservative include methylparaben, ethylparaben, propylparaben, and butylparaben. The content is preferably 0.01% by mass or more, and, in respect of improving the preservative effect of on the skin cleansing composition and stability, preferably 1% by mass or less, more preferably 0.7% by mass or less, even more preferably 0.3% by mass or less in the whole composition.

One fragrance can be used alone or two or more can be used in combination. The content is preferably 0.01% by mass or more, preferably 1% by mass or less, even more preferably 0.5% by mass or less, further more preferably 0.3% by mass or less in the whole composition, in respect of giving a good smell in use and improving stability.

One ultraviolet absorber can be used alone or two or more can be used in combination. The content is preferably 5% by mass or less, more preferably 1% by mass or less, even more preferably 0.5% by mass or less, and further more preferably substantially 0% by mass in the whole composition, in respect of improving detergency and stability.

Examples of the water-soluble inorganic salt include metallic hydroxide of alkali metals and salts of ammonium with hydrochloric acid, sulfuric acid, nitric acid, phosphoric acid, triphosphoric acid, pyrophosphoric acid and carbonic acid, and include: chlorides such as sodium chloride, potassium chloride, and magnesium chloride; sulfates such as sodium sulfate, potassium sulfate, magnesium sulfate, and aluminum sulfate; and carbonates such as sodium carbonate and sodium hydrogen carbonate.

Example of the water-soluble organic salts having from 1 to 8 carbon atoms include salts of acids such as lactic acid, succinic acid, citric acid, tartaric acid, malic acid, maleic acid, and fumaric acid with alkali metal, ammonium and the like, and include monosodium citrate, disodium citrate, trisodium citrate, potassium lactate, ammonium succinate, and potassium malate. Those having 6 or less carbon atoms are more preferable, and it is also preferable to include none of amino acids and compounds that are capable of creating inner salt.

One water-soluble inorganic salt and water-soluble organic salt having from 1 to 8 carbon atoms can be used alone or two or more can be used in combination. The content is preferably 0.5% by mass or less, more preferably 0.1% by mass or less, even more preferably 0.01% by mass or less, further more preferably less than 0.001% by mass, further more preferably substantially 0% by mass in the whole composition, in respect of improving rinsability, detergency, and usability.

The skin cleansing composition of the present invention can be produced by mixing the components (A) and (B), adding the residual components, and mixing them evenly. Alternatively, raw materials which are solid at 25° C. or raw materials which cause gelling by mixing with other components at normal temperature are melted by heating or dissolved in other components which does not cause gelling. Subsequently, the mixture is cooled to 25° C., and other components are further mixed therein to be homogeneous, thereby obtaining the skin cleansing composition.

The skin cleansing composition of the present invention is preferably applied as a cleansing agent, face wash or the like. Alternatively, the skin cleansing composition of the present invention may also be impregnated into a base material such as a non-woven fabric and the like to produce a sheet-shaped article, which can be employed for wiping makeup stains or sebum stains off.

The skin cleansing composition of the present invention is preferably transparent liquid.

Being transparent refers to those having a turbidity at 25° C. of 500 NTU or less in a turbidimeter (manufactured by Eutech Instruments Pte. Ltd., TN-100), and, in respect of improving stability, the turbidity is preferably 300 NTU or less, more preferably 100 NTU or less.

Additionally, liquid refers to a state in which the viscosity at 25° C. is 20,000 mPa·s or less. Incidentally, the viscosity is measured with a B-type viscometer (rotor No. 2, 30 rpm). The viscosity at 25° C. of the skin cleansing composition of the present invention is preferably 10,000 mPa·s or less, more preferably 1,000 mPa·s or less, even more preferably 500 mPa·s or less, in respect of improving detergency.

The skin cleansing composition of the present invention is preferably an isotropic single liquid phase exhibiting a bicontinuous structure, in respect of improving rinsability, detergency, and stability. The isotropic single liquid phase exhibiting a bicontinuous structure has a continuous phase formed by both water and oil, and thus can completely remove hard-to-remove makeup cosmetics such as waterproof mascaras and can be used by washing-off. The isotropic single liquid phase exhibiting a bicontinuous structure is also an optically isotropic transparent or translucent solution having a low viscosity, specifically referring to a middle phase (or a D phase) and a sponge phase (or an L3 phase).

In the present invention, it is possible to confirm that the skin cleansing composition contains an isotropic single liquid phase exhibiting a bicontinuous structure by observation of the appearance, observation with an optical polarizing microscope, formation of a phase diagram, measurement of the self-diffusion coefficient by NMR, conductimetry, fluorescence probing using a fluorescent dye, observation with an electron microscope (TEM, SEM and the like) by the freeze fracture replica method and the like.

The cleansing composition having a bicontinuous structure has a transparent or translucent liquid appearance. Thus, it is possible to distinguish the isotropic single liquid phase exhibiting a bicontinuous structure from other solutions by appearance determination. Incidentally, being transparent referred to in the present invention means those having a turbidity at 25° C. of 500 NTU or less in a turbidimeter (manufactured by Eutech Instruments Pte. Ltd., TN-100). Additionally, liquid refers to a state in which the viscosity at 30° C. is 20,000 mPa·s or less.

When the polarization direction of two polarizing plates is placed to be perpendicular to each other, between which a sample in a transparent vessel is placed, it can be confirmed that the sample is isotropic by absence of transmission of light. Furthermore, the observation employing the optical polarization microscope enables confirming that the sample is isotropic by absence of transmission of light when the angle between the polarizing plates is 90 degrees.

When a quasi-ternary phase equilibrium diagram composed of a water phase (water and water-soluble solvent), an oil phase (oil component) and a surfactant phase (hydrophilic nonionic surfactant and lipophilic nonionic surfactant) is employed, the confirmation on the isotropy can also be achieved by finding a feature on the phase diagram, in which it is the isotropic liquid condition and it is not a region continuing from an apex of the water phase or the oil phase. However, this sometimes cannot be applicable, depending on type of the substances to be employed, formulation of the water phase, and formulation of the surfactant phase.

The measurement of the self-diffusion coefficient by NMR is the method described in details by B. Lindman et al. in J. Colloid Interface Sci. 1981, 83, 569. The measurement of the electric conductivity is the method described in details by M. Clausse et al. in "microemulsion Systems" Marcel Dekker, New York, 1987, 387. The measurement via the fluorescent probe method employing the fluorochrome is the method described in details by B. K. Mishra et al. in Colloid Surface 1991, 56, 229.

The electron microscope observation via the freeze fracture replica method provides an image that a water phase and an oil phase form a continuous phase. Specifically, a structural body, in which a wholly rounded section and a moderately flat section are entangled to provide a net-like feature or a layered structural body, in which a wholly rounded section and a moderately flat section are continued in disorder manner are observed. This observation can provide a confirmation that this is not a microemulsion, in which only the water phase or only the oil phase forms a continuous phase.

In order to confirm that the cleansing composition has a bicontinuous structure in a simplest method, a condition in which the water phase and the oil phase form a continuous phase is employed. In the method, a liquid prepared by dissolving a water-soluble dye in water and a liquid prepared by dissolving an oil-soluble dye in oil are added to a test liquid left to stand; and after leaving the test liquid for all night and all day, the confirmation can be achieved by the coloration condition presented by the test liquid. The color of the water-soluble dye is presented when the water phase forms the continuous phase. The color of the oil-soluble dye is presented when the oil phase forms the continuous phase. Both colors of the water-soluble dye and the oil-soluble dye are presented for the composition having a bicontinuous structure.

In connection with the aforementioned embodiments, the present invention further discloses the following compositions.

<1> A skin cleansing composition comprising the following components (A), (B), (C), (D), (E), and (F):

(A) from 0.5 to 20% by mass of an oil agent having a viscosity at 30° C. of more than 30 mPa·s, (B) from 0.5 to 20% by mass of an oil agent having a viscosity at 30° C. of 30 mPa·s or less, (C) from 1 to 15% by mass of a nonionic surfactant having an HLB of 10 or more and having a residue obtained by removing a hydrogen atom from at least one hydroxyl group in sugar, reducing sugar, or polyglycerin as a hydrophilic group.

(D) from 1 to 15% by mass of a nonionic surfactant having an HLB of 8 or less, (E) from 10 to 60% by mass of a polyhydric alcohol, and (F) from 10 to 50% by mass of water, where the mass ratio of the component (A) to the component (B), (A)/(B), is from 0.05 to 30.

<2> The skin cleansing composition according to <1>, where the component (A) oil agent has a viscosity at 30° C. of preferably 40 mPa·s or more, more preferably 50 mPa·s or more, even more preferably 80 mPa·s or more, preferably 20,000 mPa·s or less, more preferably 10,000 mPa·s or less, even more preferably 1,000 mPa·s or less, further more preferably 200 mPa·s or less.

<3> The skin cleansing composition according to <1> or <2>, where the component (A) oil agent has an average molecular weight of preferably from 350 to 950, more preferably from 375 to 700, even more preferably from 400 to 600.

<4> The skin cleansing composition according to any one of <1> to <3>, where the component (A) oil agent is preferably a hydrocarbon oil having a viscosity at 30° C. of more than 30 mPa·s, an ester oil, an ether oil, a silicone oil, or an animal or plant oil, more preferably a hydrocarbon oil having a viscosity at 30° C. of more than 30 mPa·s, even more preferably liquid paraffin or hydrogenated polybutene having a viscosity at 30° C. of more than 30 mPa·s.

<5> The skin cleansing composition according to any one of <1> to <4>, where the content of the component (A) is preferably 2% by mass or more, more preferably 3.5% by mass or more, preferably 14% by mass or less, more preferably 10% by mass or less in the whole composition.

<6> The skin cleansing composition according to any one of <1> to <4>, where the content of the component (A) is preferably 1% by mass or more, preferably 18.6% by mass or less in the whole composition.

<7> The skin cleansing composition according to any one of <1> to <6>, where the component (B) oil agent has a viscosity at 30° C. of preferably 2 mPa·s or more, more preferably 3 mPa·s or more, even more preferably 4 mPa·s or more, preferably 25 mPa·s or less, more preferably 20 mPa·s or less, even more preferably 15 mPa·s or less.

<8> The skin cleansing composition according to any one of <1> to <6>, where the component (B) oil agent has a viscosity at 30° C. of preferably 27 mPa·s or less.

<9> The skin cleansing composition according to any one of <1> to <8>, where the component (B) oil agent has an average molecular weight of preferably 330 or less, more preferably from 100 to 315, even more preferably from 200 to 300.

<10> The skin cleansing composition according to any one of <1> to <9>, where the component (B) oil agent is preferably a hydrocarbon oil having a viscosity at 30° C. of 30 mPa·s or less, a monoester oil; a diester oil, a triester oil, an ether oil, or a methylcyclopolysiloxane, more preferably a hydrocarbon oil, a monoester oil, or an ether oil, even more preferably a monoester oil or an ether oil, further more preferably a monoester oil.

<11> The skin cleansing composition according to any one of <1> to <10>, where the component (B) is preferably isononyl isononanoate, tri(caprylic/capric acid) glycerin, dicaprylyl ether, or decamethylcyclopentasiloxane, more preferably isononyl isononanoate or dicaprylyl ether, even more preferably isononyl isononanoate.

<12> The skin cleansing composition according to any one of <1> to <11>, where the content of the component (B) is preferably 1.2% by mass or more, more preferably 2% by mass or more, preferably 10% by mass or less, more preferably 8% by mass or less in the whole composition.

<13> The skin cleansing composition according to any one of <1> to <11>, where the content of the component (B) is preferably 1% by mass or more, preferably 11.5% by mass or less in the whole composition.

<14> The skin cleansing composition according to any one of <1> to <13>, where the component (A) is a hydrocarbon oil, and the component (B) is a monoester oil or an ether oil.

<15> The skin cleansing composition according to any one of <1> to <14>, where the mass ratio of the component (A) to the component (B), (A)/(B), is preferably 0.25 or more, more preferably 0.5 or more, preferably 8 or less, more preferably 5 or less.

<16> The skin cleansing composition according to any one of <1> to <14>, where the mass ratio of the component (A) to the component (B), (A)/(B), is preferably 0.1 or more, preferably 9 or less.

<17> The skin cleansing composition according to any one of <1> to <16>, where the total mass of the whole oil agents including the components (A) and (B) is preferably 3% by mass or more, more preferably 4% by mass or more, even more preferably 6% by mass or more, preferably 35% by mass or less, more preferably 24% by mass or less, even more preferably 18% by mass or less in the whole composition.

<18> The skin cleansing composition according to any one of <1> to <17>, where the component (C) nonionic surfactant is preferably a polyglycerin fatty acid ester, a polyglycerin alkyl ether, a sucrose fatty acid ester, or an alkyl polyglucoside, more preferably an ester of polyglycerin and a fatty acid having from 8 to 22 carbon atoms, an ether of polyglycerin and an alkyl group having from 8 to 22 carbon atoms, an ester of a fatty acid having from 8 to 22 carbon atoms and sucrose, or an alkyl polyglucoside having an alkyl group having from 8 to 22 carbon atoms and having a degree of condensation of glucoside units of from 1 to 7.

<19> The skin cleansing composition according to any one of <1> to <18>, where the component (C) nonionic surfactant preferably has a residue obtained by removing a hydrogen atom from at least one hydroxyl group in sugar, more preferably an alkyl polyglucoside, even more preferably decyl polyglucoside.

<20> The skin cleansing composition according to any one of <1> to <19>, where the component (C) nonionic surfactant has an HLB of preferably from 10 to 20, more preferably an HLB of from 12 to 19, even more preferably an HLB of from 14 to 18.

<21> The skin cleansing composition according to any one of <1> to <20>, where the content of the component (C) is preferably 1.25% by mass or more, more preferably 1.5% by mass or more, preferably 8% by mass or less, more preferably 6% by mass or less, even more preferably 4.5% by mass or less in the whole composition.

<22> The skin cleansing composition according to any one of <1> to <20>, where the content of the component (C) is preferably 1.1% by mass or more, preferably 6.3% by mass or less in the whole composition.

<23> The skin cleansing composition according to any one of <1> to <22>, where the component (D) nonionic surfactant has an HLB of preferably from 3 to 8, more preferably an HLB of from 4 to 8, even more preferably an HLB from 5 to 8.

<24> The skin cleansing composition according to any one of <1> to <23>, where the component (D) nonionic surfactant preferably has a glycerin structure, more preferably a monoglycerin monofatty acid ester, a polyglycerin monofatty acid ester, or a monoglycerin monoalkyl ether, even more preferably, a polyglycerin monofatty acid ester or a monoglycerin monoalkyl ether, further more preferably a polyglycerin monofatty acid ester.

<25> The skin cleansing composition according to any one of <1> to <24>, where the component (D) nonionic surfactant is preferably diglyceryl monooleate, diglyceryl monoisostearate, or monoisostearyl glyceryl ether, more preferably diglyceryl monoisostearate.

<26> The skin cleansing composition according to any one of <1> to <25>, where the content of the component (D) is preferably 2% by mass or more, more preferably 2.8% by mass or more, even more preferably 3% by mass or more, preferably 12% by mass or less, more preferably 9% by mass or less, even more preferably 6% by mass or less in the whole composition.

<27> The skin cleansing composition according to any one of <1> to <25>, where the content of the component (D) is preferably 2.7% by mass or more, preferably 9.7% by mass or less in the whole composition.

<28> The skin cleansing composition according to any one of <1> to <27>, where the mass ratio of the component (A) to the component (D), (A)/(D), is preferably 0.1 or more, more preferably 0.5 or more, even more preferably 0.7 or more, preferably 2.1 or less, more preferably 2.0 or less, further more preferably 1.9 or less.

<29> The skin cleansing composition according to any one of <1> to <27>, where the mass ratio of the component (A) to the component (D), (A)/(D), is preferably 0.2 or more, preferably 2.3 or less.

<30> The skin cleansing composition according to any one of <1> to <29>, where the component (E) polyhydric alcohol is preferably 1,3-butylene glycol, glycerin, sorbitol, a glycerin derivative represented by the formula (1), or a glycerin derivative represented by the formula (2):

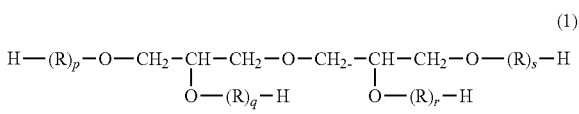

where R represents —[CH$_2$CH(CH$_3$)O]—, p, q, r, and s each represent an integer of from 0 to 20, and p+q+r+s represents an integer of from 4 to 20,

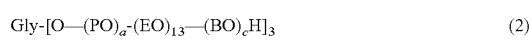

where Gly represents a residue obtained by removing hydroxyl groups from glycerin, PO represents an oxypropylene group, EO represents an oxyethylene group, a and b are the average addition mole number of each PO and EU and represent a value of from 1 to 50, the mass ratio of PO to EO, PO/EO, is from 1/5 to 5/1, BO represents an oxyalkylene group having 4 carbon atoms, and c is the average addition mole number of BO and represents a value of from 1 to 5, and where 1,3-butylene glycol, glycerin, and a glycerin derivative represented by the formula (1) are more preferable.

<31> The skin cleansing composition according to any one of <1> to <30>, where the component (E) polyhydric alcohol is preferably polyoxypropylene (9) diglyceryl ether, polyoxypropylene (14) diglyceryl ether, or polyoxybutylene polyoxyethylene polyoxypropylene glyceryl ether (3BO) (8EO) (5PO).

<32> The skin cleansing composition according to any one of <1> to <31>, where the content of the component (E) is preferably 17% by mass or more, more preferably 20% by mass or more, even more preferably 30% by mass or more, preferably 48% by mass or less, more preferably 47% by mass or less, even more preferably 46% by mass or less in the whole composition.

<33> The skin cleansing composition according to any one of <1> to <31>, where the content of the component (E) is preferably 16% by mass or more, preferably 50.3% by mass or less in the whole composition.

<34> The skin cleansing composition according to any one of <1> to <33>, where the content of the component (F) water is preferably from 17 to 45% by mass, more preferably from 18 to 35% by mass in the whole composition.

<35> The skin cleansing composition according to any one of <1> to <34>, further comprising (G) a nonionic surfactant having an HLB of 10 or more and having a polyoxyethylene chain as a hydrophilic group (except the component (C)).

<36> The skin cleansing composition according to <35>, where the component (G) has an HLB of preferably from 10 to 20, more preferably from 10 to 17, even more preferably from 10.5 to 15.

<37> The skin cleansing composition according to <35> or <36>, where the component (G) is preferably a polyoxyethylene monofatty acid ester, a polyoxyethylene glycerin fatty acid ester, a tetrafatty acid polyoxyethylene sorbit, or a polyoxyethylene sorbitan fatty acid ester, more preferably a polyoxyethylene monofatty acid ester, a polyoxyethylene glycerin fatty acid ester, or a tetrafatty acid polyoxyethylene sorbit, even more preferably polyoxyethylene (12) monolaurate ester, polyoxyethylene (7) coconut oil fatty acid glycerin, or tetraoleic acid polyoxyethylene (30) sorbit, further more preferably polyoxyethylene (12) monolaurate ester or tetraoleic acid polyoxyethylene (30) sorbit.

<38> The skin cleansing composition according to any one of <35> to <37>, where the content of the component (G) is preferably 4% by mass or more, more preferably 50 by mass or more, even more preferably 9% by mass or more, preferably 45% by mass or less, more preferably 28% by mass or less, even more preferably 25% by mass or less in the whole composition.

<39> The skin cleansing composition according to any one of <35> to <37>, where the content of the component (G) is preferably 4.2% by mass or more, preferably 30.2% by mass or less in the whole composition.

<40> The skin cleansing composition according to any one of <35> to <39>, where the total mass of the components (C), (D), and (G) is preferably 7% by mass or more, more preferably 9% by mass or more, even more preferably 15% by mass or more, preferably 50% by mass or less, more preferably 40% by mass or less, even more preferably 30% by mass or less in the whole composition.

<41> The skin cleansing composition according to any one of <35> to <39>, where the total mass of the components (C), (D), and (G) is preferably 8% by mass or more, preferably 46% by mass or less in the whole composition.

<42> The skin cleansing composition according to any one of <35> to <41>, where, as the nonionic surfactant, the components (C), (D), and (G) are preferably comprised in combination, the combination of the component (C): alkyl polyglucoside, the component (D): a monoglycerin monofatty acid ester, a polyglycerin monofatty acid ester, a monoglycerin monoalkyl ether, and the component (G): a polyoxyethylene monofatty acid ester, a tetrafatty acid polyoxyethylene sorbit is preferable, the combination of the component (C): an alkyl polyglucoside, the component (D): a polyglycerin monofatty acid ester, and the component (G): a polyoxyethylene monofatty acid ester, a tetrafatty acid polyoxyethylene sorbit is more preferable, and the combination of the component (C): decyl polyglucoside, the component (D): diglyceryl monoisostearate, and the component (G): polyoxyethylene (12) laurate ester, tetraoleic acid polyoxyethylene (30) sorbit is even more preferable.

<43> The skin cleansing composition according to any one of <35> to <42>, where the ratio of the total mass of the components (A) and (B) to the total mass of the components (C), (D), and (G), ((A)+(B))/((C)+(D)+(G)), is preferably 0.1 or more, more preferably 0.21 or more, even more preferably 0.23 or more, further more preferably 0.25 or more, preferably 1.5 or less, more preferably 1.3 or less, even more preferably 1.2 or less, further more preferably 0.8 or less.

<44> The skin cleansing composition according to any one of <35> to <42>, where the ratio of the total mass of the components (A) and (B) to the total mass of the components (C), (D), and (G), ((A)+(B))/((C)+(D)+(G)), is preferably 0.22 or more, preferably 1.4 or less.

<45> The skin cleansing composition according to any one of <35> to <44>, where the content of a nonionic surfactant other than the components (C), (D), and (G) is preferably 5% by mass or less, more preferably 3% by mass or less, even more preferably 1% by mass or less, further more preferably 0.5% by mass or less, further more preferably substantially 0% by mass in the whole composition.

<46> The skin cleansing composition according to any one of <1> to <45>, where the content of oils and fats in the form of paste or wax at 30° C. is preferably 1% by mass or less, more preferably 0.5% by mass or less, even more preferably 0.1% by mass or less, further more preferably substantially 0% by mass in the whole composition.

<47> The skin cleansing composition according to any one of <1> to <46>, where the content of a water-soluble thickener is preferably 0.5% by mass or less, more preferably 0.1% by mass or less, even more preferably less than 0.05% by mass, further more preferably 0.01% by mass or less, further more preferably substantially 0% by mass in the whole composition.

<48> The skin cleansing composition according to any one of <1> to <47>, where the content of an anionic surfactant, a cationic surfactant, and an amphoteric surfactant is preferably 1% by mass or less, more preferably 0.5% by mass or less, even more preferably 0.1% by mass or less, further more preferably substantially 0% by mass in the whole composition.

<49> The skin cleansing composition according to any one of <1> to <48>, where the content of ethanol is preferably 5% by mass or less, more preferably 3% by mass or less, even more preferably 1% by mass or less, further more preferably 0.5% by mass or less, further more preferably substantially 0% by mass in the whole composition.

<50> The skin cleansing composition according to any one of <1> to <49>, where the composition is preferably transparent liquid.

<51> The skin cleansing composition according to any one of <1> to <50>, where the viscosity at 25° C. is preferably 20,000 mPa·s or less, preferably 10,000 mPa·s or less, more preferably 1,000 mPa·s or less, even more preferably 500 mPa·s or less.

<52> The skin cleansing composition according to any one of <1> to <51>, comprising an isotropic single liquid phase exhibiting a bicontinuous structure.

<53> A skin cleansing composition comprising the following components (A), (B), (C), (D), (E), (F), and (G):

(A) from 0.5 to 20% by mass of an oil agent having a viscosity at 30° C. of more than 30 mPa·s, (B) from 0.5 to 20% by mass of an oil agent having a viscosity at 30° C. of 30 mPa·s or less, (C) from 1 to 15% by mass of a nonionic surfactant having an HLB of 10 or more and having a residue obtained by removing a hydrogen atom from at least one hydroxyl group in sugar, reducing sugar, or polyglycerin as a hydrophilic group, (D) from 1 to 15% by mass of a nonionic surfactant having an HLB of 8 or less, (E) from 10 to 60% by mass of a polyhydric alcohol, (F) from 10 to 50% by mass of water, and (G) from 4 to 45% by mass of a nonionic surfactant having an HLB of 10 or more and having a polyoxyethylene chain as a hydrophilic group, where the mass ratio of the component (A) to the component (B), (A)/(B), is from 0.05 to 30, and the ratio of the total mass of the components (A) and (B) to the total mass of the components (C), (D), and (G), ((A)B)/((C)+(D)+(G)), is from 0.1 to 1.5.

Second Embodiment

When a makeup remover is blended with a makeup cosmetic, the remover can be lightly extended at first, whereas the remover may become gradually difficult to extend. Even when a conventional makeup remover including the inventions described in prior literatures such as Patent Literatures 3 to 5 is used in such a case, the remover became gradually difficult to extend while blended with the makeup cosmetic, and extension could not be improved.

Accordingly, a makeup remover is required, which does not become difficult to extend when blended with a makeup cosmetic, can be sufficiently blended with the makeup cosmetic, and can completely remove the makeup cosmetic from the skin.

The present inventors have found that a skin cleansing composition can be obtained, which does not become difficult to extend when blended with stains such as a makeup cosmetic, can be sufficiently blended with the makeup cosmetic, and can completely remove the makeup cosmetic from the skin by using a specific glycerin derivative, a liquid oil agent, a specific nonionic surfactant, and water in combination at a specific ratio.

The skin cleansing composition of the present invention does not become difficult to extend even if blended with stains such as a makeup cosmetic, can be sufficiently blended with the makeup cosmetic, and can completely remove the makeup cosmetic from the skin. Additionally, the composition has excellent detergency and satisfactory rinsability.

The glycerin derivative of the component (H) used in the present invention are selected from the group consisting of the above (h1) and (h2).

Of the component (H), (h1) the glycerin derivative represented by the formula (1) can be obtained by addition polymerizing propylene oxide to diglycerin by a routine method. As for the number of moles of propylene oxide added, propylene oxide is added in an amount of preferably from 4 to 20 moles, more preferably from 5 to 15 moles, even more preferably from 8 to 15 moles, further more preferably from 8 to 10 moles per diglycerin molecule, in respect of reducing a stickiness feeling and improving a moist feeling.

As (h1), polyoxypropylene (9) diglyceryl ether and polyoxypropylene (14) diglyceryl ether are preferable, polyoxypropylene (9) diglyceryl ether is more preferable.

Also commercially available products such as SY-DP9 and SY-DP14 (both manufactured by SAKAMOTO YAKUHIN KOGYO CO., LTD.) can be used.

Of the component (H), (h2) the glycerin derivative represented by the formula (2) can be obtained by adding propylene oxide and ethylene oxide to glycerin, each in a ratio of from 3 to 150 molar equivalents to glycerin followed by adding alkylene oxide having 4 carbon atoms to the glycerin in a ratio of from 3 to 15 molar equivalents to the glycerin. That is, the glycerin derivative of the formula (2) can be obtained by synthesizing an adduct of PO and EO first followed by adding alkylene oxide having 4 carbon atoms in the form of block.

The mass ratio of propylene oxide (PO) to ethylene oxide (EO), (PO/EO) is from 1/5 to 5/1 in respect of improving detergency and a moist feeling, and propylene oxide and ethylene oxide may be added either in the random form or in the block form. In respect of improving detergency and a moist feeling, addition in the random form is preferable.

The average addition mole number of each of propylene oxide (PO) and ethylene oxide (EO) is 1 or more and 50 or less, preferably in the range of from 1 to 50, in respect of improving detergency and a moist feeling.

The average addition mole number of alkylene oxide having 4 carbon atoms (BO) is 1 or more and 5 or less, preferably in the range of from 1 to 5, in respect of improving detergency and a moist feeling.

Examples of the alkylene oxide having 4 carbon atoms include 1,2-butylene oxide, 2,3-butylene oxide, and tetramethylene oxide (tetrahydrofuran). Of these, 1,2-butylene oxide is preferable in respect of availability and ease of reaction control.

Usually, when these alkylene oxides are added to glycerin, an alkali catalyst, a phase transfer catalyst, a Lewis acid catalyst or the like is used to conduct addition reaction. It is generally preferable to use an alkali catalyst such as potassium hydroxide.

Specific examples of the component (h2) include those having an average addition mole number of (EO) of 8, an average addition mole number of (PO) of 5, and an average addition mole number of (BO) of 3, and polyoxybutylene polyoxyethylene polyoxypropylene glyceryl ether (3BO)(8EO)(5PO) is preferable in respect of improving detergency and a moist feeling. Commercially available products such as WILBRIDE S-753 (manufactured by NOF CORPORATION) can be used.

One or more components (H), which are selected from the group consisting of (h1) and (h2), can be used. The content is 0.05% by mass or more, preferably 0.08% by mass or more, more preferably 0.15% by mass or more, even more preferably 0.2% by mass or more, and 10% by mass or less, preferably 8% by mass or less, more preferably 3% by mass or less, even more preferable 2% by mass or less in the whole composition, in respect of improving stability. The content of the component (H) is from 0.05 to 10% by mass, preferably from 0.08 to 8% by mass, more preferably from 0.15 to 3% by mass, even more preferably from 0.2 to 2% by mass in the whole composition.

The content of the component (H) is preferably 0.07% by mass or more, preferably 8.5% by mass or less in the whole composition.

The component (I) oil agent used in the present invention is liquid at 30° C. Here, the liquid refers to those having fluidity, including paste.

The component (I) oil agent has a viscosity at 30° C. of preferably from 1 to 1,000 m Pa·s, more preferably from 2 to 100 mPa·s, even more preferably from 3 to 70 mPa·s, further more preferably from 5 to 50 m Pa·s in respect of improving detergency and stability.

The viscosity of the component (I) represents the viscosity of a mixed oil agent when two or more oil agents are mixed.

Incidentally, the viscosity of oil agent in the present invention is measured using a B-type viscometer (TV-B type, manufactured by Tokyo Keiki Inc.) with the rotor No. 1 at the number of revolutions of 60 rpm for a viscosity of less than 100 mPa·s, with the rotor No. 1 at the number of revolutions of 12 rpm for a viscosity of 100 mPa·s or more and less than 500 mPa·s, with the rotor No. 1 at the number of revolutions of 6 rpm for a viscosity of 500 mPa·s or more and less than 1,000 mPa·s, with the rotor No. 3 at the number of revolutions of 12 rpm for a viscosity of 1,000 mPa·s or more and less than 10,000 mPa·s, and with the rotor No. 4 at the number of revolutions of 12 rpm for a viscosity of 10,000 mPa·s or more.

Examples of the component (I) oil agent include hydrocarbon oils such as liquid paraffin, light liquid isoparaffin, hydrogenated polybutene, and squalane; monoester oils such as isopropyl palmitate, isopropyl myristate, octyldodecyl myristate, cetyl 2-ethylhexanoate, isononyl isononanoate, and isotridecyl isononanoate; diester oils such as neopentyl glycol dicaprate; triester oils such as tri(2-ethylhexanoate) glycerin and tri(caprylic/capric acid) glycerin; ether oils such as alkyl-1,3-dimethylbuthyl ether and dicaprylyl ether; methylcyclopolysiloxanes such as decamethylcyclopentasiloxane and octamethylcyclotetrasiloxane; and methylpolysiloxanes such as dimethylpolysiloxane.

As the component (I), in respect of improving the detergency and stability, an oil agent having a viscosity at 30° C. of 30 mPa·s or less is preferably contained, an oil agent having a viscosity at 30° C. of from 3 to 20 mPa·s is more preferable, and an oil agent having a viscosity at 30° C. of from 4 to 15 mPa·s is even more preferably contained.

The content of the oil agent having a viscosity at 30° C. of 30 mPa·s or less in the component (I) is preferably from 10 to 90% by mass, more preferably from 15 to 60.% by mass, even more preferably from 25 to 50%; by mass.

As the component (I), an oil agent having a viscosity at 30° C. of 30 mPa·s or less and an oil agent having a viscosity at 30° C. of more than 30 mPa·s are preferably used in combination, in respect of improving rinsability, retention of a moist feeling, and stability.

When an oil agent having a viscosity at 30° C. of 30 mPa·s or less and an oil agent having a viscosity at 30° C. of more than 30 mPa·s are used in combination, the oil agent having a viscosity at 30° C. of more than 30 mPa·s has a viscosity at 30° C. of preferably from 35 to 20,000 m Pa·s, more preferably from 40 to 10,000 mPa·s, even more preferably from 50 to 1,000 mPa·s, further more preferably from 80 to 200 mPa·s, in respect of improving rinsability, detergency, and stability.

As the component (I), in respect of improving the detergency and stability, a monoester oil and a hydrocarbon oil are preferably combined. As the monoester oil, those having a viscosity at 30° C. of 30 mPa·s or less are preferable, those having a viscosity at 30° C. of from 3 to 20 mPa·s are more preferable, those having a viscosity at 30° C. of from 4 to 15 mPa·s are even more preferable. As the hydrocarbon oil, those having a viscosity at 30° C. of more than 30 mPa·s are preferable, those having a viscosity at 30° C. of from 50 to 200 mPa·s are more preferable, and those having a viscosity at 30° C. of from 80 to 150 mPa·s are even more preferable.

As the component (I), a monoester oil having a viscosity at 30° C. of from 4 to 15 mPa·s and a hydrocarbon oil having a viscosity at 30° C. of from 80 to 150 mPa·s are preferably used in combination.

As the component (I) oil agent, commercially available products, for example, HICALL K-350 (115 mPa·s, manufactured by KANEDA Co., Ltd.) as liquid paraffin, PARLEAM 18 (18160 mPa·s, manufactured by NOF Corporation), PARLEAM 6 (33 mPa·s, manufactured by NOF Corporation), PARLEAM 4 (5 mPa·s, manufactured by NOF Corporation), PARLEAM EX (17 mPa·s, manufactured by NOF Corporation) and the like as hydrogenated polybutene; MARUKASOL R (5 mPa·s, manufactured by Maruzen Petrochemical Co., Ltd.), IP solvents 1620 and 2028 (both manufactured by Idemitsu Petrochemical Co., Ltd.), Isopar L and Isopar H (both manufactured by Exxon Mobil Chemical Company), Isosol 300 and 400 (both manufactured by Shin-Nippon Petrochemical Co., Ltd.) and the like as light liquid isoparaffin; Cetiol OE (5 mPa·s, manufactured by BASF) as dicaprylyl ether; ASE166K (8 mPa·s, manufactured by Kao Corporation) as 1,3-dimethylbuthyl ether; SALACOS 99 (7.4 mPa·s, manufactured by Nisshin Oil Mills, Ltd.) as isononyl isononanoate; EXEPARL IPM (10 mPa·s, manufactured by Kao Corporation) as isopropyl myristate; EXEPARL IPP (10 mPa·s, manufactured by Kao Corporation) as isopropyl palmitate; COCONARD MT (27 mPa·s, manufactured by Kao Corporation) as tri(caprylic/capric acid) glyceryl; and Silicone SH245 (3 mPa·s, manufactured by Dow Corning Toray Co., Ltd.) as decamethylcyclotetrasiloxane can be used.

One or more components (I) can be used. The content is 3% by mass or more, preferably 4% by mass or more, more preferably 5% by mass or more, even more preferably 6% by mass or more, 35% by mass or less, preferably 25% by mass or less, more preferably 18% by mass or less, even more preferably 15% by mass or less in the whole composition, in respect of improving rinsability, retention of a moist feeling, and stability. The content of the component (I) is from 3 to 35% by mass, preferably from 4 to 25% by mass, more preferably from 5 to 18% by mass, far more preferably from 6 to 15% by mass in the whole composition.

The content of the component (I) is preferably 30% by mass or less in the whole composition.

In the present invention, the mass ratio of the component (H) to the component (I), ((H)/(I)), is preferably 0.001 or more, more preferably 0.009 or more, even more preferably 0.02 or more, preferably 1 or less, more preferably 0.8 or less, even more preferably 0.3 or less, in respect of improving spreadability one minute after application, rinsability, detergency, and retention of a moist feeling and reducing a remaining feeling. The mass ratio of the component (H) to the component (I), ((H)/(I)), is preferably from 0.001 to 1, more preferably from 0.009 to 0.8, even more preferably from 0.02 to 0.3.

The mass ratio of the component (H) to the component (I), ((H)/(I)), is preferably 0.007 or more, preferably 0.85 or less.

The component (J) nonionic surfactant used in the present invention is selected from the group consisting of (j1), (j2), and (j3).

Of the component (J), the component (j1) nonionic surfactant has a residue obtained by removing a hydrogen atom from at least one hydroxyl group in sugar, reducing sugar, or polyglycerin as a hydrophilic group, and examples thereof include polyglycerin fatty acid esters, polyglycerin alkyl ethers, sucrose fatty acid esters, and alkyl polyglucosides.

As the polyglycerin fatty acid ester, esters of polyglycerin and a fatty acid having from 8 to 22 carbon atoms are preferable in respect of improving rinsability, detergency, and stability, and examples thereof include polyglycerin octanoate ester, polyglycerin 2-ethylhexanoate ester, polyglycerin decanoate ester, polyglycerin laurate ester, polyglycerin myristate ester, polyglycerin palmitate ester, polyglycerin isostearate ester, polyglycerin stearate ester, polyglycerin oleate ester, and polyglycerin behenate ester. Of these, monoesters of a polyglycerin having a degree of polymerization of from 3 to 15 and a fatty acid having from 12 to 18 carbon atoms are preferable, monoesters of a polyglycerin having a degree of polymerization of from 8 to 12 and a fatty acid having from 12 to 18 carbon atoms are more preferable, and monoesters of polyglycerin having a degree of polymerization of from 8 to 12 and a fatty acid having from 12 to 14 carbon atoms are even more preferable.

As the polyglycerin alkyl ether, ethers of a polyglycerin and an alkyl group having from 8 to 22 carbon atoms are preferable in respect of improving rinsability, detergency, and stability, and examples thereof include polyglycerin octyl ether, polyglycerin decyl ether, polyglycerin lauryl ether, polyglycerin myristyl ether, polyglycerin palmityl ether, polyglycerin isostearyl ether, polyglycerin stearyl ether, polyglycerin oleyl ether, and polyglycerin behenyl ether. Of these, monoethers of a polyglycerin having a degree of polymerization of from 3 to 15 and an alkyl group having from 12 to 18 carbon atoms are preferable, monoethers of a polyglycerin having a degree of polymerization of from 8 to 12 and a fatty acid having from 12 to 18 carbon atoms are more preferable, and monoethers of polyglycerin having a degree of polymerization of from B to 12 and a fatty acid having from 12 to 14 carbon atoms are even more preferable.

As the sucrose fatty acid ester, esters of a fatty acid having from 8 to 22 carbon atoms and sucrose are preferable in respect of improving rinsability, detergency, and stability, and examples thereof include sucrose octanoate ester, sucrose 2-ethylhexanoate ester, sucrose decanoate ester, sucrose laurate ester, sucrose myristate ester, sucrose palmitate ester, sucrose isostearate ester, sucrose stearate ester, sucrose oleate ester, and sucrose behenate ester. Of these, monoesters of a fatty acid having from 12 to 18 carbon atoms and sucrose are more preferable, and sucrose laurate ester and sucrose stearate ester are even more preferable.

As the alkyl polyglucoside, those having an alkyl group of from 8 to 22 carbon atoms and having a degree of condensation of glucoside units of from 1 to 7 are preferable in respect of improving rinsability, detergency, and stability, and examples thereof include octyl polyglucoside, 2-ethylhexyl polyglucoside, decyl polyglucoside, lauryl polyglucoside, myristyl polyglucoside, palmityl polyglucoside, isostearyl polyglucoside, stearyl lauryl polyglucoside, oleyl polyglucoside, and behenyl polyglucoside. Of these, as the alkyl polyglucoside, those having an alkyl group of from 8 to 11 carbon atoms and having a degree of condensation of glucoside units of from 1 to 1.4 and those having an alkyl group of from 12 to 14 carbon atoms and having a degree of condensation of glucoside units of from 1.5 to 4.0 are more preferable, and decyl polyglucoside is even more preferable.

As the component (11), commercially available products such as Sunsoft Q-12S (HLB: 15.5, manufactured by Taiyo Kagaku Co., Ltd.) and Sunsoft M-12J (HLB: 15.5, manufactured by Taiyo Kagaku Co., Ltd.) as polyglycerin (10) monolaurate ester, Sunsoft Q-14S (HLB: 14.5, manufactured by Taiyo Kagaku Co., Ltd.) as polyglycerin (10) monomyristate ester, and MYDOL 10 (HLB: 17, active ingredient content 40% by mass, manufactured by Kao Corporation) as decyl polyglucoside can be used.

As the component (11) nonionic surfactant, those having a residue obtained by removing a hydrogen atom from at least one hydroxyl group in sugar are preferable in respect of improving rinsability, detergency, and stability and further in respect that the skin cleansing composition takes an isotropic single liquid phase exhibiting a bicontinuous structure described below, alkyl polyglucosides are more preferable, and decyl polyglucoside is even more preferable.

The component (11) nonionic surfactant has an HLB of 10 or more, and the HLB is preferably from 10 to 20, more preferably from 12 to 19, even more preferably from 14 to 18 in respect of improving rinsability, detergency, and stability.

The HLB (Hydrophilic-Lipophilic Balance) herein indicates the molecular weight of the hydrophilic group moiety relative to the total molecular weight of the surfactant, and the HLB for polyoxyethylenic nonionic surfactants can be determined according to Griffin's formula shown below:

$$\text{HLB value} = E/5$$

E: % by mass of the polyoxyethylene moiety contained in the surfactant molecule

One or more components (j1) can be used. The content is preferably 1% by mass or more, more preferably 1.25% by mass or more, even more preferably 1.5% by mass or more, preferably 20% by mass or less, more preferably 8% by mass or less, even more preferable 6% by mass or less, further more preferably 4.5% by mass or less in the whole composition, in respect of improving rinsability, detergency, and stability and further in respect that the skin cleansing composition takes an isotropic single liquid phase exhibiting a bicontinuous structure described below. The content of the component (j1) is preferably from 1 to 20% by mass, more preferably from 1 to 8% by mass, even more preferably from 1.25 to 6% by mass, further more preferably from 1.5 to 4.5% by mass in the whole composition.

The content of the component (j1) is preferably 1.1% by mass or more, preferably 6.3% by mass or less in the whole composition.

Of the component (J), the component (j2) nonionic surfactant has an HLB of 8 or less, and the HLB is preferably from 3 to 8, more preferably from 4 to 8, even more preferably from 5 to 8 in respect of improving rinsability, detergency, and stability and further in respect that the skin cleansing composition takes an isotropic single liquid phase exhibiting a bicontinuous structure described below.

Specific examples thereof include monoglycerin monofatty acid esters such as monoglyceryl monoisostearate; polyglycerin monofatty acid esters such as diglyceryl monooleate and diglyceryl monoisostearate; polyglycerin monoalkyl ethers such as 2-ethylhexyl diglyceryl ether, monoglycerin monoalkyl ethers such as monoisostearyl glyceryl ether; and polyoxyethylene monofatty acid esters such as polyoxyethylene (5) monostearate ester.

As the component (j2), those having a glycerin structure are preferable in respect of improving rinsability, detergency, and stability and further in respect that the skin cleansing composition takes an isotropic single liquid phase exhibiting a bicontinuous structure described below. Monoglycerin monofatty acid esters, polyglycerin monofatty acid esters, and monoglycerin monoalkyl ethers are preferable, polyglycerin monofatty acid esters and monoglycerin monoalkyl ethers are more preferable, and polyglycerin monofatty acid esters are even more preferable.

Diglyceryl monooleate, diglyceryl monoisostearate, and monoisostearyl glyceryl ether are preferable, and diglyceryl monoisostearate is more preferable.

As the component (j2), commercially available products such as PENETOL GE-IS (HLB: 5, manufactured by Kao Corporation) as monoisostearyl glyceryl ether, POEM DO-100V (HLB: 7, manufactured by RIKEN VITAMIN Co., Ltd.) as diglyceryl monooleate, and Cosmol 41V (HLB: 8, manufactured by The Nisshin 011110 Group, Ltd.) as diglyceryl monoisostearate can be used.

One or more components (j2) can be used. The content is preferably 1% by mass or more, more preferably 2% by mass or more, even more preferably 2.8% by mass or more, further more preferably 3% by mass or more, preferably 15% by mass or less, more preferably 12% by mass or less, even more preferably 9% by mass or less, further more preferably 6% by mass or less in the whole composition, in respect of improving rinsability, detergency, and stability. The content of the component (j2) is preferably from 1 to 15% by mass, more preferably from 2 to 12% by mass, even more preferably from 2.8 to 9% by mass, further more preferably from 3 to 6% by mass in the whole composition.

The content of the component (j2) is preferably 2.7% by mass or more, preferably 9.7% by mass or less in the whole composition.

Of the component (J), the component (j3) nonionic surfactant is a nonionic surfactant having an HLB of 10 or more and having a polyoxyethylene chain as a hydrophilic group (except the component (j1)) and can improve the rinsability, detergency, and stability. The component (j3) preferably has an HLB of from 10 to 20, more preferably from 10 to 17, even more preferably from 10.5 to 15, in respect of improving rinsability, detergency, and stability and further in respect that the skin cleansing composition takes an isotropic single liquid phase exhibiting a bicontinuous structure described below.

Specific examples thereof include polyoxyethylene monofatty acid esters such as polyoxyethylene (12) monolaurate ester, tetrafatty acid polyoxyethylene sorbit such as tetraoleic acid polyoxyethylene (30) sorbit, polyoxyethylene glycerin fatty acid esters such as polyoxyethylene (7) coconut oil fatty acid glycerin, polyoxyethylene alkyl ethers such as polyoxyethylene (20) octyldodecyl ether, polyoxyethylene alkylphenyl ethers such as polyoxyethylene (20) nonylphenyl ether, polyoxyethylene castor oil derivatives such as polyoxyethylene (50) castor oil, polyoxyethylene hydrogenated castor oil derivatives such as polyoxyethylene (60) hydrogenated castor oil monoisolaurate, and polyoxyethylene sorbitan fatty acid esters such as polyoxyethylene (20) sorbitan monostearate ester and polyoxyethylene (30) sorbitan tristearate ester. Additionally, of these, those having 8 or more carbon atoms in the hydrophobic group are preferable, and those having 12 or more carbon atoms in the hydrophobic group are more preferable, in respect of improving rinsability.

As the component (j3), polyoxyethylene monofatty acid esters, polyoxyethylene glycerin fatty acid esters, tetrafatty acid polyoxyethylene sorbit, and polyoxyethylene sorbitan fatty acid esters are preferable, polyoxyethylene monofatty acid esters, polyoxyethylene glycerin fatty acid esters, tetrafatty acid polyoxyethylene sorbit are more preferable, polyoxyethylene (12) monolaurate ester, polyoxyethylene (7) coconut oil fatty acid glycerin, and tetraoleic acid polyoxyethylene (30) sorbit are even more preferable, polyoxyethylene (12) monolaurate ester and tetraoleic acid polyoxyethylene (30) sorbit are further more preferable, in respect of improving the stability, rinsability, and detergency, and further in respect that the skin cleansing composition takes an isotropic single liquid phase exhibiting a bicontinuous structure described below.

As the component (j3), commercially available products, such as EMANON 1112 (HLB: 13.7, manufactured by Kao Corporation) as polyoxyethylene (12) monolaurate ester; RHEODOL 430V (HLB: 10.5, manufactured by Kao Corporation) as tetraoleic acid polyoxyethylene (30) sorbit; LEVENOL C301 (HLB: 13, manufactured by Kao Corporation) as polyoxyethylene coconut oil fatty acid glycerin; and RHEODOL TW-0320V (HLB:11, manufactured by Kao Corporation) as polyoxyethylene (20) sorbitan tristearate also can be used.

One or more components (j3) can be used. The content is preferably 3% by mass or more, more preferably 5% by mass or more, even more preferably 9% by mass or more, preferably 45% by mass or less, more preferably 28% by mass or less, even more preferably 25% by mass or less in the whole composition, in respect of improving rinsability, detergency, and stability. The content of the component (j3) is preferably from 3 to 45% by mass, more preferably from 5 to 28% by mass, even more preferably from 9 to 25% by mass in the whole composition.

The content of the component (j3) is preferably 4.2% by mass or more, preferably 30.2% by mass or less in the whole composition.

In the present invention, the component (J) is selected from the group consisting of the components (j1), (j2), and (j3) and includes at least the components (j1) and (j2). The content of the component (J), that is, the total mass of the components (j1), (j2), and (j3) is 5% by mass or more, preferably 9% by mass or more, more preferably 15% by mass or more, 50% by mass or less, preferably 40% by mass or less, more preferably 30% by mass or less in the whole composition, in respect of improving the spreadability one minute after application, rinsability, and detergency and reducing the remaining feeling and further in respect that the skin cleansing composition takes an isotropic single liquid phase exhibiting a bicontinuous structure described below. The total mass of the components (j1), (j2), and (j3) is from 5 to 50% by mass, preferably from 9 to 40% by mass, and more preferably from 15 to 30% by mass of the whole composition.

The total mass of the components (j1), (j2), and (j3) is preferably 8% by mass or more, preferably 46% by mass or less in the whole composition.

The skin cleansing composition of the present invention preferably contains the components (j1), (j2), and (j3) in combination as a nonionic surfactant, in respect of taking an isotropic single liquid phase exhibiting a bicontinuous structure described below. As the combination of the components (j1), (j2), and (j3), in respect of improving rinsability, detergency, and stability, the combination of the component (j1): an alkyl polyglucoside, the component (j2): a monoglycerin monofatty acid ester, a polyglycerin monofatty acid ester, a monoglycerin monoalkyl ether, and the component (j3): a polyoxyethylene monofatty acid ester, a tetrafatty acid polyoxyethylene sorbit is preferable, the combination of the component (j1): an alkyl polyglucoside, the component (j2): a polyglycerin monofatty acid ester, and the component (j3): a polyoxyethylene monofatty acid ester, a tetrafatty acid polyoxyethylene sorbit is more preferable, the combination of the component (j1): decyl polyglucoside, the component (j2): diglyceryl monoisostearate, and the component (j3): polyoxyethylene (12) laurate ester, tetraoleic acid polyoxyethylene (30) sorbit is even more preferable.

In the present invention, the mass ratio of the component (H) to the component (J) (the total mass of the components (j1), (j2), and (j3)), ((H)/(J)), is 0.001 or more, preferably 0.004 or more, more preferably 0.005 or more, even more preferably 0.011 or more, 0.5 or less, preferably 0.35 or less, more preferably 0.15 or less, even more preferably 0.08 or less, in respect of improving spreadability one minute after application, rinsability, and detergency and reducing a remaining feeling, and further in respect that the skin cleansing composition takes an isotropic single liquid phase exhibiting a bicontinuous structure described below. The mass ratio of the component (H) to the component (J), ((H)/(J)), is from 0.001 to 0.5, preferably from 0.004 to 0.35, more preferably from 0.005 to 0.15, even more preferably from 0.011 to 0.08.

The mass ratio of the component (H) to the component (J), ((H)/(J)), is preferably 0.003 or more, preferably 0.4 or less.

The mass ratio of the component (I) to the component (J) (the total mass of the components (j1), (j2), and (j3)), ((I)/(J)), is preferably 0.1 or more, more preferably 0.21 or more, even more preferably 0.25 or more, preferably 1.5 or less, more preferably 1.2 or less, even more preferably 0.8 or less, in respect of improving the spreadability one minute after application, rinsability, and detergency and reducing the remaining feeling, and further in respect that the skin cleansing composition takes an isotropic single liquid phase exhibiting a bicontinuous structure described below. The mass ratio of the component (I) to the component (J), ((I)/(J)), is preferably from 0.1 to 1.5, more preferably from 0.21 to 1.2, even more preferably from 0.25 to 0.8.

The mass ratio of the component (I) to the component (J), ((I)/(J)), is preferably 0.22 or more, preferably 1.4 or less.

The content of the component (K) water is from 10 to 50% by mass, preferably from 17 to 45% by mass, more preferably from 18 to 35% by mass in the whole composition, in respect of improving rinsability, detergency, stability, and usability.

The skin cleansing composition of the present invention can further contain (L) a polyhydric alcohol other than the component (H), thereby being able to improve rinsability, detergency, stability, and retention of a moist feeling.

The component (L) polyhydric alcohol is those used in common skin cleansing compositions, and examples thereof include 1,3-butylene glycol, propylene glycol, glycerin, sorbitol, diglycerin, dipropylene glycol, 1,3-propanediol, polyoxyethylene methyl glucoside, and polyethylene glycols having a number average molecular weight of 2,000 or less.

Of these, 1,3-butylene glycol, glycerin, and sorbitol are preferable, and 1,3-butylene glycol and glycerin are more preferable, in respect of improving rinsability, detergency, stability, and retention of a moist feeling.

One or more components (L) can be used. The content is preferably 10% by mass or more, more preferably 16% by mass or more, even more preferably 20% by mass or more, further more preferably 25% by mass or more, preferably 60% by mass or less, more preferably 55% by mass or less, even more preferably 50% by mass or less, further more preferably 45% by mass or less in the whole composition, in respect of improving rinsability, detergency, stability, and retention of a moist feeling. The content of the component (L) is preferably from 10 to 60% by mass, more preferably from 16 to 55% by mass, even more preferably from 20 to 50% by mass, further more preferably from 25 to 45% by mass in the whole composition.

The content of the component (L) is preferably 15.5% by mass or more, preferably 45.6% by mass or less in the whole composition.

The skin cleansing composition of the present invention may further contain components usually used in cleansing agents, for example, a nonionic surfactant other than components (j1), (j2), and (j3), oils and fats in the form of paste or wax at 30° C., a water-soluble thickener, an anionic surfactant, a cationic surfactant, an amphoteric surfactant, ethanol, a bactericide, a moisturizing agent other than the component (H), a colorant, a preservative, a texture improver, a fragrance, an anti-inflammatory agent, a whitening agent, an antiperspirant, an ultraviolet absorber, a water-soluble inorganic salt, a water-soluble organic salt having from 1 to 8 carbon atoms and the like.

One or more nonionic surfactants other than components (j1), (j2), and (j3) can be used in combination. The content is preferably 5% by mass or less, more preferably 3% by mass or less, even more preferably 1% by mass or less, further more preferably 0.5% by mass or less, further more preferably substantially 0% by mass in the whole composition, in respect of improving rinsability, detergency, and stability.

One or more oils and fats in the form of paste or wax at 30° C. can be used in combination. The content is preferably 1% by mass or less, more preferably 0.5% by mass or less, even more preferably 0.1% by mass or less, further more preferably substantially 0% by mass in the whole composition, in respect of improving rinsability, detergency, and stability.

As the water-soluble thickener, one or more selected from the group consisting of acrylate polymers comprising, as the constituent unit, acrylic acid or methacrylic acid, polysaccharide such as pullulan, cellulosic polymer, and polyethylene glycols having a weight average molecular weight of 200,000 or more and 5,000,000 or less can be used in combination.

The acrylate polymers are those synthesized by using acrylic acid or methacrylic acid, for example, as the monomer, and examples thereof include carboxyvinyl polymers and acrylic acid-alkyl methacrylate copolymers. Acrylic acid-alkyl methacrylate copolymers are preferable, and copolymers of acrylic acid and an alkyl methacrylate having from 10 to 30 carbon atoms ((acrylic acid/alkyl acrylate (C10-30)) copolymers) are more preferable. Examples of commercially available products include PEMULEN TR-1, PEMULEN TR-2, and Carbopol ETD2020 (manufactured by Lubrizol Advanced Materials).

Examples of the polysaccharide include pullulan and sodium hyaluronate. Examples of the cellulosic polymer include methyl cellulose, ethyl cellulose, hydroxyethyl cellulose, hydroxypropyl cellulose, hydroxypropyl methyl cellulose, and sodium carboxymethyl cellulose.

The weight average molecular weight of the polyethylene glycol as the thickener is preferably 200,000 or more, more preferably 300,000 or more, far more preferably 500,000 or more, even more preferably 1,000,000 or more, further more preferably 2,000,000 or more, preferably 5,000,000 or less, more preferably 4,000,000 or less, far more preferably 3,500,000 or less. Examples of the commercially available product include ALKOX series (Meisel Chemical Works, Ltd., polyethylene glycol): ALKOX E30 (weight average molecular weight: from 300,000 to 500,000), ALKOX E-45 (weight average molecular weight: from 600,000 to 800, 000), ALKOX E-60 (weight average molecular weight: from 1,000,000 to 1,200,000), ALKOX E-75 (weight average molecular weight: from 2,000,000 to 2,500,000), and ALKOX E-100 (weight average molecular weight: from 2,500,000 to 3,000,000).

One or more water-soluble thickeners can be used in combination. The content is preferably 0.5% by mass or less, more preferably 0.1% by mass or less, far more preferably less than 0.05% by mass, still even preferably 0.01% by mass or less, further more preferably substantially 0% by mass in the whole composition, in respect of improving rinsability, detergency, and usability.

One or more anionic surfactants, cationic surfactants, and amphoteric surfactants can be used in combination. The content is preferably 1% by mass or less, more preferably 0.5% by mass or less, far more preferably 0.1% by mass or less, even more preferably substantially 0% by mass in the whole composition, in respect of improving rinsability, detergency, and stability.

In order to spread the skin cleansing composition evenly, the content of ethanol is preferably 5% by mass or less, more preferably 3% by mass or less, far more preferably 1% by mass or less, even more preferably 0.5% by mass or less, further more preferably substantially 0% by mass in the whole composition.

One or more preservatives can be used in combination. Examples of an oil-base preservative include methylparaben, ethylparaben, propylparaben, and butylparaben. The content is preferably 0.01% by mass or more, preferably 1% by mass or less, more preferably 0.7% by mass or less, even more preferably 0.3% by mass or less in the whole composition, in respect of improving the preservative effect of on the skin cleansing composition and stability.

One or more fragrances can be used in combination. The content is preferably 0.01% by mass or more, preferably 1% by mass or less, more preferably 0.5% by mass or less, even more preferably 0.3% by mass or less in the whole composition, in respect of giving a good smell in use and improving the stability.

One or more ultraviolet absorbers can be used in combination. The content is preferably 5% by mass or less, more preferably 1% by mass or less, even more preferably 0.5% by mass or less, further more preferably substantially 0% by mass in the whole composition, in respect of improving the detergency and stability.

Examples of the water-soluble inorganic salt include metallic hydroxide of alkali metals and salts of ammonium with hydrochloric acid, sulfuric acid, nitric acid, phosphoric acid, triphosphoric acid, pyrophosphoric acid and carbonic acid, and include: chlorides such as sodium chloride, potassium chloride, and magnesium chloride; sulfates such as sodium sulfate, potassium sulfate, magnesium sulfate, and aluminum sulfate; and carbonates such as sodium carbonate and sodium hydrogen carbonate.

Example of the water-soluble organic salts having from 1 to 8 carbon atoms include salts of acids such as lactic acid, succinic acid, citric acid, tartaric acid, malic acid, maleic acid, and fumaric acid with alkali metal, ammonium and the like, and include monosodium citrate, disodium citrate, trisodium citrate, potassium lactate, ammonium succinate, and potassium malate. The compound having 6 or less carbon atoms is more preferable, and it is also preferable to contain none of amino acids and compounds that are capable of creating inner salt.

One or more water-soluble inorganic salts and water-soluble organic salts having from 1 to 8 carbon atoms can be used in combination. The content is preferably 0.50 by mass or less, more preferably 0.1% by mass or less, even more preferably 0.01% by mass or less, even more preferably less than 0.001% by mass, further more preferably substantially 0% by mass in the whole composition, in respect of improving rinsability, detergency, and usability.

The skin cleansing composition of the present invention can be produced by homogeneously mixing all the components by a routine method. Alternatively, raw materials which are solid at 25° C. or raw materials which cause gelling by mixing with other components at normal temperature are melted by heating or dissolved in other components which does not cause gelling. Subsequently, the mixture is cooled to 25° C., and other components are further mixed therein to be homogeneous, thereby obtaining the skin cleansing composition.

The skin cleansing composition of the present invention is preferably applied as a cleansing agent, face wash or the like. Alternatively, the skin cleansing composition of the present invention may also be impregnated into a base material such as a non-woven fabric and the like to produce a sheet-shaped article, which can be employed for wiping makeup stains or sebum stains off.

The skin cleansing composition of the present invention is preferably transparent liquid.

Being transparent refers to having a turbidity at 25° C. of 500 NTU or less in a turbidimeter (manufactured by Eutech Instruments Pte. Ltd., TN-100), and, in respect of improving the stability, the turbidity is preferably 300 NTU or less, more preferably 100 NTU or less.

Additionally, liquid refers to a state in which the viscosity at 25° C. is 20,000 mPa·s or less. Incidentally, the viscosity is measured with a B-type viscometer (rotor No. 2, 30 rpm). The viscosity at 25° C. of the composition of the present invention is preferably 10,000 mPa·s or less, more preferably 1,000 mPa·s or less, even more preferably 500 mPa·s or less, in respect of improving detergency.

The skin cleansing composition of the present invention is preferably an isotropic single liquid phase exhibiting a bicontinuous structure, in respect of improving rinsability, detergency, and stability. The isotropic single liquid phase exhibiting a bicontinuous structure has a continuous phase formed by both water and oil, and thus can completely remove hard-to-remove makeup cosmetics such as waterproof mascaras and can be used by washing-off. The isotropic single liquid phase exhibiting a bicontinuous structure is also an optically isotropic transparent or translucent solution having a low viscosity, specifically referring to a middle phase (or a D phase) and a sponge phase (or an L3 phase).

In the present invention, it is possible to confirm that the skin cleansing composition contains an isotropic single liquid phase exhibiting a bicontinuous structure by observation of appearance, observation with an optical polarizing microscope, formation of a phase diagram, measurement of the self-diffusion coefficient by NMR, conductimetry, fluorescence probing using a fluorescent dye, observation with an electron microscope (TEM, SEM and the like) by the freeze fracture replica method and the like.

The cleansing composition having a bicontinuous structure has a transparent or translucent liquid appearance. Thus, it is possible to distinguish the isotropic single liquid phase exhibiting a bicontinuous structure from other solutions by appearance determination. Incidentally, being transparent referred to in the present invention means those having a turbidity at 25° C. of 500 NTU or less in a turbidimeter (manufactured by Eutech Instruments Pte. Ltd., TN-100).

Additionally, liquid refers to a state in which the viscosity at 30° C. is 20,000 mPa·s or less.

When the polarization direction of two polarizing plates is adjusted to be mutually perpendicular, between which a sample in a transparent vessel is placed, the sample can be confirmed to be isotropic by absence of transmission of light. Further, the observation employing the optical polarization microscope allows confirmation that the sample is isotropic by absence of transmission of light when the angle between the polarizing plates is 90 degrees.

When a quasi-ternary phase equilibrium diagram composed of a water phase (water and water-soluble solvent), an oil phase (oil component) and a surfactant phase (hydrophilic nonionic surfactant and lipophilic nonionic surfactant) is employed, the confirmation on the isotropy can be achieved by finding a feature on the phase diagram, in which it is the isotropic liquid condition and it is not a region continuing from an apex of the water phase or the oil phase. However, this sometimes may not be applicable, depending on type of the substances to be employed, formulation of the water phase, and formulation of the surfactant phase.

The measurement of the self-diffusion coefficient via NMR is the method described in details by B. Lindman et al., in J. Colloid Interface Sci., 1981, 83, 569. The measurement of the electric conductivity is the method described in details by M. Clausse et al., in "Microemulsion Systems" Marcel Dekker, New York, 1987, 387. The measurement via the fluorescent probe method employing the fluorochrome is the method described in details by B. K. Mishra et al., in Colloid Surface 1991, 56, 229.

The electron microscope observation via the freeze fracture replica method provides an image that a water phase and an oil phase form a continuous phase. Specifically, a structural body, in which a wholly rounded section and a moderately flat section are entangled to provide a net-like feature or a layered structural body, in which a wholly rounded section and a moderately flat section are continued in disorder manner are observed. This observation can provide a confirmation that this is not a microemulsion, in which only the water phase or only the oil phase forms a continuous phase.

In order to confirm that the cleansing composition exhibits a bicontinuous structure in a simplest method, a condition in which the water phase and the oil phase form a continuous phase is employed. In the method, a liquid prepared by dissolving a water-soluble dye in water and a liquid prepared by dissolving an oil-soluble dye in oil are added to a test liquid left to stand; and after leaving the test liquid for all night and all day, the confirmation can be achieved by the coloration condition presented by the test liquid. The color of the water-soluble dye is presented when the water phase forms the continuous phase. The color of the oil-soluble dye is presented when the oil phase forms the continuous phase. Both colors of the water-soluble dye and the oil-soluble dye are presented for the composition having a bicontinuous structure.

In connection with the aforementioned embodiments, the present invention further discloses the following compositions.

<54> A skin cleansing composition comprising the following components (H), (I), (J), and (K):

(H) from 0.05 to 10% by mass of one or more glycerin derivatives selected from the group consisting of (h1) and (h2):

(h1) the formula (1)

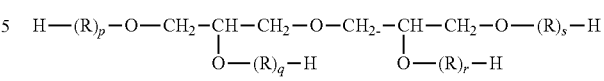

where R represents —[CH$_2$CH(CH$_3$)O]—, p, q, r, and s each represent an integer of from 0 to 20, and p+q+r+s represents an integer of from 4 to 20, (h2) the formula (2)

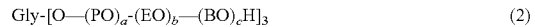

where Gly represents a residue obtained by removing hydroxyl groups from glycerin, PD represents an oxypropylene group, EO represents an oxyethylene group, a and b are the average addition mole number of each PO and EO and represent a value of from 1 to 50, the mass ratio of PO to EO, PO/EO, is from 1/5 to 5/1, BO represents an oxyalkylene group having 4 carbon atoms, and c is the average addition mole number of BO and represents a value of from 1 to 5, (I) from 3 to 35% by mass of an oil agent which is liquid at 30° C., (J) from 5 to 50% by mass of a nonionic surfactant selected from the group consisting of (j1), (j2), and (j3) and comprising at least (j1) and (j2), (j1) a nonionic surfactant having an HLB of 10 or more and having a residue obtained by removing a hydrogen atom from at least one hydroxyl group in sugar, reducing sugar, or polyglycerin as a hydrophilic group, (j2) a nonionic surfactant having an HLB of 8 or less, and (j3) a nonionic surfactant having an HLB of 10 or more and having a polyoxyethylene chain as a hydrophilic group, and (K) from 10 to 50% by mass of water, where the mass ratio of the component (H) to (J), ((H)/(J)), is from 0.001 to 0.5.

<55> The skin cleansing composition according to <54>, where, of the component (H), (h1) the glycerin derivative represented by the formula (1) is preferably polyoxypropylene (9) diglyceryl ether or polyoxypropylene (14) diglyceryl ether, more preferably polyoxypropylene (9) diglyceryl ether.

<56> The skin cleansing composition according to <54> or <55>, where, of the component (H), (h2) the glycerin derivative represented by the formula (2) preferably has an average addition mole number of (EO) of 8, an average addition mole number of (PO) of 5, and an average addition mole number of (BO) of 3, more preferably polyoxybutylene polyoxyethylene polyoxypropylene glyceryl ether (3BO) (8EO) (5PO).

<57> The skin cleansing composition according to any one of <54> to <56>, where the content of the component (H) is preferably 0.08% by mass or more, more preferably 0.15% by mass or more, even more preferably 0.2% by mass or more, preferably 8% by mass or less, more preferably 3% by mass or less, even more preferably 2% by mass or less in the whole composition.

<58> The skin cleansing composition according to any one of <54> to <56>, where the content of the component (H) is preferably 0.07% by mass or more, preferably 8.5% by mass or less in the whole composition.

<59> The skin cleansing composition according to any one of <54> to <58>, where the component (I) oil agent has a viscosity at 30° C. of preferably from 1 to 1,000 mPa·s, more preferably from 2 to 100 mPa·s, even more preferably from 3 to 70 mPa·s, further more preferably from 5 to 50 mPa·s.

<60> The skin cleansing composition according to any one of <54> to <59>, where the component (I) oil agent is preferably a hydrocarbon oil, a monoester oil, a diester oil, a triester oil, an ether oil, a methylcyclopolysiloxane, or a methylpolysiloxane.

<61> The skin cleansing composition according to any one of <54> to <60>, where the component (I) oil agent comprises preferably an oil agent having a viscosity at 30° C. of 30 mPa·s or less, more preferably an oil agent having a viscosity at 30° C. of from 3 to 20 mPa·s or less, even more preferably an oil agent having a viscosity at 30° C. of from 4 to 15 mPa·s or less.

<62> The skin cleansing composition according to any one of <54> to <61>, where the component (I) oil agent comprises preferably from 10 to 90% by mass of, more preferably from 15 to 60% by mass of, even more preferable from 25 to 50% by mass of an oil agent having a viscosity at 30° C. of 30 mPa·s or less in the component (I).

<63> The skin cleansing composition according to any one of <54> to <62>, where the component (I) oil agent used is a combination of preferably an oil agent having a viscosity at 30° C. of 30 mPa·s or less and an oil agent having a viscosity at 30° C. of more than 30 mPa·s, and the oil agent having a viscosity at 30° C. of more than 30 mPa·s has a viscosity at 30° C. of preferably from 35 to 20,000 mPa·s, more preferably from 40 to 10,000 mPa·s, even more preferably from 50 to 1,000 mPa·s, further more preferably from 80 to 200 mPa·s.

<64> The skin cleansing composition according to any one of <54> to <63>, where the component (I) is preferably a combination of a monoester oil and a hydrocarbon oil, the monoester oil is one having a viscosity at 30° C. of preferably 30 mPa·s or less, more preferably from 3 to 20 mPa·s, even more preferably from 4 to 15 mPa·s, and the hydrocarbon oil is one having a viscosity at 30° C. of preferably more than 30 mPa·s, more preferably from 50 to 200 mPa·s, even more preferably from 80 to 150 mPa·s.

<65> The skin cleansing composition according to any one of <54> to <64>, where the component (I) used is preferably a combination of a monoester oil having a viscosity at 30° C. of from 4 to 15 mPa·s and a hydrocarbon oil having a viscosity at 30° C. of from 80 to 150 mPa·s.

<66> The skin cleansing composition according to any one of <54> to <65>, where the content of the component (I) is preferably 4% by mass or more, more preferably 5% by mass or more, even more preferably 6% by mass or more, preferably 25% by mass or less, more preferably 18% by mass or less, even more preferably 15% by mass or less in the whole composition.

<67> The skin cleansing composition according to any one of <54> to <65>, where the content of the component (I) is preferably 30% by mass or less in the whole composition.

<68> The skin cleansing composition according to any one of <54> to <67>, where the mass ratio of the component (H) to the component (I), ((H)/(I)), is preferably 0.001 or more, more preferably 0.009 or more, even more preferably 0.02 or more, preferably 1 or less, more preferably 0.8 or less, even more preferably 0.3 or less.

<69> The skin cleansing composition according to any one of <54> to <67>, where the mass ratio of the component (H) to the component (I), ((H)/(I)), is preferably 0.007 or more, preferably 0.85 or less.

<70> The skin cleansing composition according to any one of <54> to <69>, where, of the component (J), the component (j1) nonionic surfactant is preferably a polyglycerin fatty acid ester, a polyglycerin alkyl ether, a sucrose fatty acid ester, or an alkyl polyglucoside, more preferably an ester of polyglycerin and a fatty acid having from 8 to 22 carbon atoms, an ether of polyglycerin and an alkyl group having from 8 to 22 carbon atoms, an ester of a fatty acid having from 8 to 22 carbon atoms and sucrose, or an alkyl polyglucoside having an alkyl group having from 8 to 22 carbon atoms and having a degree of condensation of glucoside units of from 1 to 7.

<71> The skin cleansing composition according to any one of <54> to <70>, where the component (j1) nonionic surfactant preferably has a residue obtained by removing a hydrogen atom from at least one hydroxyl group in sugar, more preferably an alkyl polyglucoside, even more preferably decyl polyglucoside.

<72> The skin cleansing composition according to any one of <54> to <71>, where the component (j1) nonionic surfactant has an HLB of preferably from 10 to 20, more preferably an HLB of from 12 to 19, and even more preferably an HLB of from 14 to 18.

<73> The skin cleansing composition according to any one of <54> to <72>, where the content of the component (j1) is preferably 1% by mass or more, more preferably 1.25% by mass or more, even more preferably 1.5% by mass or more, preferably 20% by mass or less, more preferably 8% by mass or less, even more preferably 64 by mass or less, further more preferably 4.5% by mass or less in the whole composition.

<74> The skin cleansing composition according to any one of <54> to <72>, where the content of the component (j1) is preferably 1.1% by mass or more, preferably 6.3% by mass or less in the whole composition.

<75> The skin cleansing composition according to any one of <54> to <74>, where, of the component (J), the component (j2) nonionic surfactant has an HLB of preferably from 3 to 8, more preferably an HLB of from 4 to 8, even more preferably an HLB of from 5 to 8.

<76> The skin cleansing composition according to any one of <54> to <75>, where the component (j2) nonionic surfactant preferably has a glycerin structure, preferably a monoglycerin monofatty acid ester, a polyglycerin monofatty acid ester, or a monoglycerin monoalkyl ether, more preferably, a polyglycerin monofatty acid ester or a monoglycerin monoalkyl ether, even more preferably a polyglycerin monofatty acid ester.

<77> The skin cleansing composition according to any one of <54> to <76>, where the component (j2) nonionic surfactant is preferably diglyceryl monooleate, diglyceryl monoisostearate, or monoisostearyl glyceryl ether, more preferably diglyceryl monoisostearate.

<78> The skin cleansing composition according to any one of <54> to <77>, where the content of the component (j2) is preferably 1% by mass or more, more preferably 2% by mass or more, far more preferably 2.8% by mass or more, even more preferably 3% by mass or more, preferably 15% by mass or less, more preferably 12% by mass or less, even more preferably 9% by mass or less, further more preferably 6% by mass or less in the whole composition.

<79> The skin cleansing composition according to any one of <54> to <77>, where the content of the component (j2) is preferably 2.7% by mass or more, preferably 9.7% by mass or less in the whole composition.

<80> The skin cleansing composition according to any one of <54> to <79>, where, of the component (J), the component (j3) nonionic surfactant has an HLB of preferably from 10 to 20, more preferably an HLB of from 10 to 17, even more preferably an HLB of from 10.5 to 15.

<81> The skin cleansing composition according to any one of <54> to <80>, where the component (j3) nonionic surfactant is preferably a polyoxyethylene monofatty acid ester, a polyoxyethylene glycerin fatty acid ester, a tetrafatty acid polyoxyethylene sorbit, or polyoxyethylene sorbitan fatty acid ester, more preferably a polyoxyethylene monofatty acid ester, a polyoxyethylene glycerin fatty acid ester, or a tetrafatty acid polyoxyethylene sorbit, even more preferably polyoxyethylene (12) monolaurate ester, polyoxyethylene (7) glyceryl cocoate, or tetraoleic acid polyoxyethylene (30) sorbit, further more preferably polyoxyethylene (12) monolaurate ester or tetraoleic acid polyoxyethylene (30) sorbit.

<82> The skin cleansing composition according to any one of <54> to <81>, where the content of the component (j3) is preferably 3% by mass or more, more preferably 5% by mass or more, even more preferably 9% by mass or more, preferably 45% by mass or less, more preferably 28% by mass or less, even more preferably 25% by mass or less in the whole composition.

<83> The skin cleansing composition according to any one of <54> to <81>, where the content of the component (j3) is preferably 4.2% by mass or more, preferably 30.2% by mass or less in the whole composition.

<84> The skin cleansing composition according to any one of <54> to <83>, where the content of the component (J), that is, the total mass of the components (j1), (j2), and (j3) is preferably 9% by mass or more, more preferably 15% by mass or more, preferably 40% by mass or less, more preferably 30% by mass or less in the whole composition.

<85> The skin cleansing composition according to any one of <54> to <83>, where the total mass of the components (j1), (j2), and (j3) preferably 8% by mass or more, preferably 46% by mass or less in the whole composition.

<86> The skin cleansing composition according to any one of <54> to <85>, where the component (J) nonionic surfactant comprises preferably the components (j1), (j2), and (j3) in combination, and where the combination of the component (j1): alkyl polyglucoside, the component (j2): a monoglycerin monofatty acid ester, a polyglycerin monofatty acid ester, a monoglycerin monoalkyl ether, and the component (j3): a polyoxyethylene monofatty acid ester, a tetrafatty acid polyoxyethylene sorbit is preferable, the combination of the component (j1): alkyl polyglucoside, the component (j2): polyglycerin monofatty acid ester, and the component (j3): a polyoxyethylene monofatty acid ester, a tetrafatty acid polyoxyethylene sorbit is more preferable, and the combination of the component (j1): decyl polyglucoside, the component (j2): diglyceryl monoisostearate, and the component (j3): polyoxyethylene (12) laurate ester, tetraoleic acid polyoxyethylene (30) sorbit is even more preferable.

<87> The skin cleansing composition according to any one of <54> to <86>, where the mass ratio of the component (H) to the component (J) (the total mass of the components (j1), (j2), and (j3)), ((H)/(J)), is preferably 0.004 or more, more preferably 0.005 or more, even more preferably 0.011 or more, preferably 0.35 or less, more preferably 0.15 or less, even more preferably 0.08 or less.

<88> The skin cleansing composition according to any one of <54> to <86>, where the mass ratio of the component (H) to the component (J), ((H)/(J)), is preferably 0.003 or more, preferably 0.4 or less.

<89> The skin cleansing composition according to any one of <54> to <88>, where the mass ratio of the component (I) to the component (J) (the total mass of the components (j1), (j2), and (j3)), ((I)/(J)), is preferably 0.1 or more, more preferably 0.21 or more, even more preferably 0.25 or more, preferably 1.5 or less, more preferably 1.2 or less, even more preferably 0.8 or less.

<90> The skin cleansing composition according to any one of <54> to <88>, where the mass ratio of the component (I) to the component (J), ((I)/(J)), is preferably 0.22 or more, preferably 1.4 or less.

<91> The skin cleansing composition according to any one of <54> to <90>, where the content of the component (K) water is preferably from 17 to 45% by mass, more preferably from 18 to 35% by mass in the whole composition.

<92> The skin cleansing composition according to any one of <54> to <91>, capable of further comprising (L) polyhydric alcohol other than the component (H).

<93> The skin cleansing composition according to <92>, where the component (L) polyhydric alcohol is preferably 1,3-butylene glycol, glycerin, or sorbitol, more preferably 1,3-butylene glycol or glycerin.

<94> The skin cleansing composition according to <92> or <93>, where the content of the component (L) is preferably 10% by mass or more, more preferably 16% by mass or more, even more preferable 20% by mass or more, further more preferably 25% by mass or more, preferably 60% by mass or less, more preferably 55% by mass or less, even more preferably 50% by mass or less, further more preferably 45% by mass or less in the whole composition.

<95> The skin cleansing composition according to <92> or <93>, where the content of the component (L) is preferably 15.5% by mass or more, preferably 45.6% by mass or less in the whole composition.

<96> The skin cleansing composition according to any one of <54> to <95>, where the content of the nonionic surfactant other than the components (j1), (j2), and (j3) is preferably 5% by mass or less, more preferably 3% by mass or less, even more preferably 1% by mass or less, still more preferably 0.5% by mass or less, further more preferably substantially 0% by mass in the whole composition.

<97> The skin cleansing composition according to any one of <54> to <96>, where the content of oils and fats in the form of paste or wax at 30° C. is preferably 1% by mass or less, more preferably 0.5% by mass or less, even more preferably 0.1% by mass or less, further more preferably substantially 0% by mass in the total composition.

<98> The skin cleansing composition according to any one of <54> to <97>, where the content of a water-soluble thickener is preferably 0.5% by mass or less, more preferably 0.1% by mass or less, even more preferably less than 0.05% by mass, still more preferably 0.01% by mass or less, further more preferably substantially 0% by mass in the whole composition.

<99> The skin cleansing composition according to any one of <54> to <98>, where the content of an anionic surfactant, a cationic surfactant, and an amphoteric surfactant is preferably 1% by mass or less, more preferably 0.5% by mass or less, even more preferably 0.1% by mass or less, further more preferably substantially 0% by mass in the whole composition.

<100> The skin cleansing composition according to any one of <54> to <99>, where the content of ethanol is preferably 5% by mass or less, more preferably 3% by mass or less, even more preferably 1% by mass or less, still more preferably 0.5% by mass or less, further more preferably substantially 0% by mass in the whole composition.

<101> The skin cleansing composition according to any one of <54> to <100>, where the composition is preferably transparent liquid.

<102> The skin cleansing composition according to any one of <54> to <101>, where the viscosity at 25° C. is preferably 20,000 mPa·s or less, preferably 10,000 mPa·s or less, more preferably 1,000 mPa·s or less, even more preferably 500 mPa·s or less.

<103> The skin cleansing composition according to any one of <54> to <102>, comprising an isotropic single liquid phase exhibiting a bicontinuous structure.

EXAMPLES

Examples 1 to 23 and Comparative Examples 1 to 6

Skin cleansing compositions having the components shown in Table 1 to Table 5 were produced and evaluated for an appearance, a feeling that fingers stop on the skin on rinsing, absence of a remaining feeling, foam retention on washing the face after makeup is removed, spreadability on application, a cleansing rate, and a moist feeling 20 minutes after cleansing. The results are shown in Table 1 to Table 4 altogether.

(Production Method)

Components (A) and (B) were mixed, and the remaining components were further added thereto and mixed evenly to thereby obtain the skin cleansing composition. When there was a component which is solid at 25° C., or when a gel-like component was generated by mixing at room temperature, the mixture was heated at from 70 to 75° C. with stirring for dissolution. After the component was sufficiently dissolved, the mixture was cooled to 25° C. to thereby obtain the skin cleansing composition.

All the skin cleansing compositions of the present invention were transparent liquid.

(Evaluation Method)

(1) Appearance:

The appearance of each skin cleansing composition was visually observed after one hour of storage at 25° C. after production.

I: monolayer.
II: bilayer.

(2) Feeling that fingers stop on the skin on rinsing:

Five expert panelists applied 0.65 mg/cm² of foundation (Sofina Primavista liquid foundation, Ocher 05 (manufactured by Kao Corporation), the same foundation was used for evaluation in the tests hereinafter) on the skin of an inner forearm to a size of 3 cm×10 cm. About two grams of each skin cleansing composition was applied thereover on the forearm, and ease of wash-off on rinsing by washing off with water was evaluated based on the following five grades. The results were indicated by the total score of the five panelists.

5: Clearly feel that fingers stop.
4: Feel that fingers stop.
3: Slightly feel that fingers stop.
2: Hardly feel that fingers stop.
1: Not feel that fingers stop at all.

(3) Absence of remaining feeling:

Five expert panelists applied 0.65 mg/cm² of the foundation on the skin of an inner forearm to a size of 3 cm×10 cm. About two grams of each skin cleansing composition was applied thereon on the forearm and rinsed by washing off with water for 20 seconds. Then, a feeling that the agent does not remain on the skin was evaluated based on the following five grades. The results were indicated by the total score of the five panelists.

5: There is clearly no remaining feeling.
4: There is no remaining feeling.
3: There is a slight remaining feeling.
2: There is a remaining feeling.
1: There is a clearly remaining feeling.

(4) Foam retention on washing the face after makeup is removed:

Each skin cleansing composition was pipetted, 1 mL was dropped on a Teflon (registered trademark) plate (5 cm×8 cm), and applied so as to extend to a diameter of 3 cm. After two seconds, the entire Teflon (registered trademark) plate was slowly immersed in water and removed out after two seconds. The operation was repeated three times. Thereafter, the Teflon (registered trademark) plate was inclined for three seconds such that the wider side was perpendicular to the ground to remove the moisture. Subsequently, one push amount (1 g) of Blare Marshmallow Whip Rich Moisture (manufactured by Kao Corporation) was placed on the area of the aforementioned plate to which the skin cleansing composition was applied and blended by fingers at a rate of one stroke per second. The number of blending strokes until the foam were decreased and 500 of the plate surface was exposed was determined.

(5) Spreadability on Application:

Five expert panelists applied 0.65 mg/cm² of the foundation on the skin of an inner forearm to a size of 3 cm×10 cm. Two grams of each skin cleansing composition was applied thereover. The area was massaged in the direction from the elbow to the wrist with a forefinger at a rate of a reciprocation per second, and spreadability was evaluated based on the following five grades. The results were indicated by the total score of the five panelists.

5: Very easy to spread.
4: Easy to spread.
3: Slightly easy to spread.
2: Difficult to spread.
1: Clearly difficult to spread.

(6) Cleansing rate:

As an oil-based mascara (waterproof mascara), 0.002 g of Kose Sports Beauty Fasio Ultracurl Lock Mascara (long) BK001 (trade name) was evenly applied on a glass slide to a circle of a diameter of 1.2 cm and left for two hours to dryness. About 0.05 g of each skin cleansing composition was placed thereon, and the oil-based mascara was massaged with fingers 50 times at a rate of three strokes per second. Then, the slide was lightly rinsed with tap water, dried for 30 minutes, and then, the weight was determined. From the weight change, the cleansing rate was determined by the following expression.

A: Weight of the glass slide (g)
B: Weight of the glass slide after application of the oil-based mascara (g)
C: Weight of the glass slide after cleansing (g)

$$\text{Cleansing rate } (\%) = \left(1 - \frac{(C-A)}{(B-A)}\right) \times 100$$

(7) Moist feeling 20 minutes after cleansing

Five expert panelists applied 1.5 g of the foundation to the entire face. About three grams of each skin cleansing composition was applied thereover on the face, blended, and then rinsed by washing off with water. A moist feeling until 20 minutes passed after the moisture was wiped off with a towel was evaluated based on the following five grades. The results were indicated by the total score of the five panelists.

5: Very moist.
4: Moist.
3: Slightly moist.
2: Not so moist.
1: Clearly not moist.

TABLE 1

| Components (% by mass) | | Example 1 | Example 2 | Example 3 | Comp. Ex. 1 | Comp. Ex. 2 | Comp. Ex. 3 | Comp. Ex. 4 |
|---|---|---|---|---|---|---|---|---|
| A | Liquid paraffin (Viscosity: 115 mPa·s, HICALL K-350, manufactured by KANEDA Co., Ltd.) | 9.00 | 6.17 | 1.00 | 10.00 | 9.90 | 0.10 | — |
| B | Isononyl isononanoate (Viscosity: 7.4 mPa·s, SALACOS 99, manufactured by Nisshin Oil Mills, Ltd.) | 1.00 | 3.83 | 9.00 | — | 0.10 | 9.90 | 10.00 |
| C | Decyl polyglucoside (HLB 17, MYDOL 10, active ingredient content 40%, manufactured by Kao Corporation) | 7.50 | 7.50 | 7.50 | 7.50 | 7.50 | 7.50 | 7.50 |
| D | Diglycerin monoisostearate (HLB 8, Cosmol 41V, manufactured by The Nisshin OilliO Group, Ltd.) | 4.60 | 4.60 | 4.60 | 4.60 | 4.60 | 4.60 | 4.60 |
| G | Tetraoleic acid polyoxyethylene (30) sorbit (HLB 10.5, RHEODOL 430V, manufactured by Kao Corporation) | 3.00 | 3.00 | 3.00 | 3.00 | 3.00 | 3.00 | 3.00 |
| | Polyoxyethylene (12) monolaurate ester (HLB 13.7, EMANON 1112, manufactured by Kao Corporation) | 11.40 | 11.40 | 11.40 | 11.40 | 11.40 | 11.40 | 11.40 |
| E | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 | 0.45 | 0.45 |
| | 1,3-Butylene glycol | 16.05 | 16.05 | 16.05 | 16.05 | 16.05 | 16.05 | 16.05 |
| | Glycerin | 23.50 | 23.50 | 23.50 | 23.50 | 23.50 | 23.50 | 23.50 |
| | Sorbitol | | | | | | | |
| F | Water | 23.25 | 23.25 | 23.25 | 23.25 | 23.25 | 23.25 | 23.25 |
| | Fragrance | 0.25 | 0.25 | 0.25 | 0.25 | 0.25 | 0.25 | 0.25 |
| Total | | 100.00 | 100.00 | 100.00 | 100.00 | 100.00 | 100.00 | 100.00 |
| Content of B/% | | 1.0 | 3.8 | 9.0 | 0.0 | 0.1 | 9.9 | 10.0 |
| Content of C/% (active ingredient content) | | 3.0 | 3.0 | 3.0 | 3.0 | 3.0 | 3.0 | 3.0 |
| Content of E/% | | 40.00 | 40.00 | 40.00 | 40.00 | 40.00 | 40.00 | 40.00 |
| Content of F/% | | 27.75 | 27.75 | 27.75 | 27.75 | 27.75 | 27.75 | 27.75 |
| Content of G/% | | 14.40 | 14.40 | 14.40 | 14.40 | 14.40 | 14.40 | 14.40 |
| Total amount of (A + B)/% | | 10.0 | 10.0 | 10.0 | 10.0 | 10.0 | 10.0 | 10.0 |
| Total amount of (C + D + G)/% | | 22.00 | 22.00 | 22.00 | 22.00 | 22.00 | 22.00 | 22.00 |
| A/B | | 9.00 | 1.61 | 0.11 | — | 99.00 | 0.01 | 0.00 |
| A/D | | 1.96 | 1.34 | 0.22 | 2.2 | 2.15 | 0.02 | — |
| (A + B)/(C + D + G) | | 0.45 | 0.45 | 0.45 | 0.45 | 0.45 | 0.45 | 0.45 |
| Appearance | | I | I | I | II | II | I | I |
| Feeling that fingers stop on the skin on rinsing | | 23 | 25 | 23 | 13 | 13 | 18 | 18 |
| Absence of remaining feeling | | 23 | 25 | 24 | 14 | 14 | 18 | 18 |
| Foam retention on washing the face after makeup is removed (strokes) | | 80 | 100 or more | 80 | 30 | 30 | 35 | 35 |
| Spreadability on application | | 23 | 25 | 25 | 18 | 18 | 22 | 22 |
| Cleansing rate (%) | | 80 | 90 | 92 | 50 | 50 | 90 | 90 |
| Moist feeling 20 minutes after cleansing | | 25 | 25 | 23 | 20 | 20 | 18 | 18 |

TABLE 2

| Components (% by mass) | | Example 4 | Example 5 | Example 2 | Example 6 | Example 7 | Example 8 | Example 9 | Example 2 | Example 10 | Example 11 |
|---|---|---|---|---|---|---|---|---|---|---|---|
| A | Liquid paraffin (Viscosity: 115 mPa·s, HICALL K-350, manufactured by KANEDA Co., Ltd.) | 3.08 | 4.32 | 6.17 | 9.87 | 18.51 | 6.17 | 6.17 | 6.17 | 6.17 | 6.17 |
| B | Isononyl isononanoate (Viscosity: 7.4 mPa·s, SALACOS 99, manufactured by Nisshin Oil Mills, Ltd.) | 1.92 | 2.68 | 3.83 | 6.13 | 11.49 | 3.83 | 3.83 | 3.83 | 3.83 | 3.83 |
| C | Decyl polyglucoside (HLB 17, MYDOL 10, active ingredient content 40%, manufactured by Kao Corporation) | 7.50 | 7.50 | 7.50 | 7.50 | 7.50 | 15.68 | 9.55 | 7.50 | 5.45 | 2.73 |
| D | Diglycerin monoisostearate (HLB 8, Cosmol 41V, manufactured by The Nisshin OilliO Group, Ltd.) | 4.60 | 4.60 | 4.60 | 5.77 | 8.50 | 9.62 | 5.85 | 4.60 | 3.35 | 2.70 |
| G | Tetraoleic acid polyoxyethylene (30) sorbit (HLB 10.5, RHEODOL 430V, manufactured by Kao Corporation) | 3.00 | 3.00 | 3.00 | 3.00 | 3.00 | 6.27 | 3.82 | 3.00 | 2.18 | 1.09 |
| | Polyoxyethylene (12) monolaurate ester (HLB 13.7, EMANON 1112, manufactured by Kao Corporation) | 11.40 | 11.40 | 11.40 | 10.23 | 7.50 | 23.84 | 14.51 | 11.40 | 8.29 | 3.12 |

TABLE 2-continued

| Components (% by mass) | | Example 4 | Example 5 | Example 2 | Example 6 | Example 7 | Example 8 | Example 9 | Example 2 | Example 10 | Example 11 |
|---|---|---|---|---|---|---|---|---|---|---|---|
| E | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 | 0.45 | 0.45 | 0.45 | 0.45 | 0.45 |
| | 1,3-Butylene glycol | 18.08 | 17.27 | 16.05 | 13.61 | 7.9 | 6.31 | 13.62 | 16.05 | 18.48 | 18 |
| | Glycerin | 26.47 | 25.28 | 23.50 | 19.94 | 11.65 | 9.24 | 19.93 | 23.50 | 27.07 | 27 |
| | Sorbitol | | | | | | | | | | |
| F | Water | 23.25 | 23.25 | 23.25 | 23.25 | 23.25 | 18.34 | 22.02 | 23.25 | 24.48 | 34.66 |
| | Fragrance | 0.25 | 0.25 | 0.25 | 0.25 | 0.25 | 0.25 | 0.25 | 0.25 | 0.25 | 0.25 |
| Total | | 100.00 | 100.00 | 100.00 | 100.00 | 100.00 | 100.00 | 100.00 | 100.00 | 100.00 | 100.00 |
| Content of B/% | | 1.9 | 2.7 | 3.8 | 6.1 | 11.5 | 3.8 | 3.8 | 3.8 | 3.8 | 3.8 |
| Content of C/% (active ingredient content) | | 3.0 | 3.0 | 3.0 | 3.0 | 3.0 | 6.3 | 3.8 | 3.0 | 2.2 | 1.1 |
| Content of E/% | | 45.00 | 43.00 | 40.00 | 34.00 | 20.00 | 16.00 | 34.00 | 40.00 | 46.00 | 45.45 |
| Content of F/% | | 27.75 | 27.75 | 27.75 | 27.75 | 27.75 | 27.75 | 27.75 | 27.75 | 27.75 | 36.30 |
| Content of G/% | | 14.40 | 14.40 | 14.40 | 13.23 | 10.50 | 30.11 | 18.33 | 14.40 | 10.47 | 4.21 |
| Total amount of (A + B)/% | | 5.00 | 7.00 | 10.00 | 16.00 | 30.00 | 10.00 | 10.00 | 10.00 | 10.00 | 10.00 |
| Total amount of (C + D + G)/% | | 22.00 | 22.00 | 22.00 | 22.00 | 22.00 | 46.00 | 28.00 | 22.00 | 16.00 | 8.00 |
| A/B | | 1.60 | 1.61 | 1.61 | 1.61 | 1.61 | 1.61 | 1.61 | 1.61 | 1.61 | 1.61 |
| A/D | | 0.67 | 0.94 | 1.34 | 1.71 | 2.18 | 0.64 | 1.05 | 1.34 | 1.84 | 2.29 |
| (A + B)/(C + D + G) | | 0.23 | 0.32 | 0.45 | 0.73 | 1.36 | 0.22 | 0.36 | 0.45 | 0.63 | 1.25 |
| Appearance | | I | I | I | I | I | I | I | I | I | I |
| Feeling that fingers stop on the skin on rinsing | | 25 | 25 | 25 | 25 | 22 | 25 | 25 | 25 | 25 | 23 |
| Absence of remaining feeling | | 25 | 25 | 25 | 25 | 22 | 23 | 25 | 25 | 25 | 23 |
| Foam retention on washing the face after makeup is removed (strokes) | | 100 or more | 100 or more | 100 or more | 100 or more | 80 | 100 or more | 100 or more | 100 or more | 100 or more | 82 |
| Spreadability on application | | 25 | 25 | 25 | 25 | 23 | 23 | 25 | 25 | 25 | 25 |
| Cleansing rate (%) | | 80 | 90 | 90 | 90 | 95 | 85 | 90 | 90 | 90 | 90 |
| Moist feeling 20 minutes after cleansing | | 25 | 25 | 25 | 25 | 23 | 25 | 25 | 25 | 25 | 25 |

TABLE 3

| Components (% by mass) | | Example 12 | Example 2 | Example 13 | Comp. Ex. 5 | Comp. Ex. 6 |
|---|---|---|---|---|---|---|
| A | Liquid paraffin (Viscosity: 115 mPa · s, HICALL K-350, manufactured by KANEDA Co., Ltd.) | 6.17 | 6.17 | 6.17 | 6.17 | 6.17 |
| B | Isononyl isononanoate (Viscosity: 7.4 mPa · s, SALACOS 99, manufactured by Nisshin Oil Mills, Ltd.) | 3.83 | 3.83 | 3.83 | 3.83 | 3.83 |
| C | Decyl polyglucoside (HLB 17, MYDOL 10, active ingredient content 40%, manufactured by Kao Corporation) | 7.50 | 7.50 | 7.50 | 7.50 | 7.50 |
| D | Diglycerin monoisostearate (HLB 8, Cosmol 41V, manufactured by The Nisshin OilliO Group, Ltd.) | 4.60 | 4.60 | 4.60 | 4.60 | 4.60 |
| G | Tetraoleic acid polyoxyethylene (30) sorbit (HLB 10.5, RHEODOL 430V, manufactured by Kao Corporation) | 3.00 | 3.00 | 3.00 | 3.00 | 3.00 |
| | Polyoxyethylene (12) monolaurate ester (HLB 13.7, EMANON 1112, manufactured by Kao Corporation) | 11.40 | 11.40 | 11.40 | 11.40 | 11.40 |
| E | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 |
| | 1,3-Butylene glycol | 20.21 | 16.05 | 7.22 | 24.28 | 3.77 |
| | Glycerin | 29.59 | 23.50 | 10.58 | 35.52 | 5.53 |
| F | Water | 13 | 23.25 | 45 | 3.00 | 53.50 |
| | Fragrance | 0.25 | 0.25 | 0.25 | 0.25 | 0.25 |
| Total | | 100.00 | 100.00 | 100.00 | 100.00 | 100.00 |
| Content of B/% | | 3.8 | 3.8 | 3.8 | 3.8 | 3.8 |
| Content of C/% (active ingredient content) | | 3.0 | 3.0 | 3.0 | 3.0 | 3.0 |
| Content of E/% | | 50.25 | 40.00 | 18.25 | 60.25 | 9.75 |
| Content of F/% | | 17.50 | 27.75 | 49.50 | 7.50 | 58.00 |
| Content of G/% | | 14.40 | 14.40 | 14.40 | 14.40 | 14.40 |
| Total amount of (A + B)/% | | 10.00 | 10.00 | 10.00 | 10.00 | 10.00 |
| Total amount of (C + D + G)/% | | 22.00 | 22.00 | 22.00 | 22.00 | 22.00 |
| A/B | | 1.61 | 1.61 | 1.61 | 1.61 | 1.61 |
| A/D | | 1.34 | 1.34 | 1.34 | 1.34 | 1.34 |

TABLE 3-continued

| Components (% by mass) | Example 12 | Example 2 | Example 13 | Comp. Ex. 5 | Comp. Ex. 6 |
|---|---|---|---|---|---|
| (A + B)/(C + D + G) | 0.45 | 0.45 | 0.45 | 0.45 | 0.45 |
| Appearance | I | I | I | II | I |
| Feeling that fingers stop on the skin on rinsing | 25 | 25 | 25 | 18 | 22 |
| Absence of remaining feeling | 25 | 25 | 25 | 17 | 22 |
| Foam retention on washing the face after makeup is removed (strokes) | 100 or more | 100 or more | 100 or more | 90 | 90 |
| Spreadability on application | 23 | 25 | 25 | 17 | 23 |
| Cleansing rate (%) | 90 | 90 | 85 | 50 | 50 |
| Moist feeling 20 minutes after cleansing | 25 | 25 | 23 | 18 | 18 |

TABLE 4

| | Components (% by mass) | Ex. 14 | Ex. 15 | Ex. 16 | Ex. 17 | Ex. 18 | Ex. 19 | Ex. 20 |
|---|---|---|---|---|---|---|---|---|
| A | Liquid paraffin (Viscosity: 115 mPa · s, HICALL K-350, manufactured by KANEDA Co., Ltd.) | 6.17 | 6.17 | 6.17 | 6.17 | 6.17 | 6.17 | 6.17 |
| B | Isononyl isononanoate (Viscosity: 7.4 mPa · s, SALACOS 99, manufactured by Nisshin Oil Mills, Ltd.) | 3.83 | 3.83 | 3.83 | 3.83 | 3.83 | 3.83 | 3.83 |
| | Tri(caprylic/capric acid)glyceryl (Viscosity 27 mPa · s, COCONARD MT, manufactured by Kao Corporation) | | | | | | | 1.00 |
| | Decamethylcyclopentasiloxane (Viscosity: 3 mPa · s, Silicone SH245, manufactured by Dow Corning Toray Co., Ltd.) | | | | | | | 1.00 |
| C | Decyl polyglucoside (HLB 17, MYDOL 10, active ingredient content 40%, manufactured by Kao Corporation) | 7.50 | 7.50 | 7.50 | 7.50 | 7.50 | 7.50 | 7.50 |
| D | Diglycerin monoisostearate (HLB 8, Cosmol 41V, manufactured by The Nisshin OilliO Group, Ltd.) | 4.60 | 5.00 | 5.00 | 4.60 | 4.60 | 4.60 | 4.60 |
| G | Tetraoleic acid polyoxyethylene (30) sorbit (HLB 10.5, RHEODOL 430V, manufactured by Kao Corporation) | 3.00 | 3.00 | 3.00 | 3.00 | 3.00 | 3.00 | 3.00 |
| | Polyoxyethylene (12) monolaurate ester (HLB 13.7, EMANON 1112, manufactured by Kao Corporation) | 11.40 | 11.00 | 11.00 | 11.40 | 11.40 | 11.40 | 11.40 |
| E | Polyoxypropylene (9) diglyceryl ether (SY-DP9, manufactured by SAKAMOTO YAKUHIN KOGYO CO., LTD.) | 0.07 | 0.25 | 4 | | | 0.45 | 0.45 |
| | Polyoxypropylene (14) diglyceryl ether (SY-DP14, manufactured by SAKAMOTO YAKUHIN KOGYO CO., LTD.) | | | | 0.45 | | | |
| | Polyoxybutylene polyoxyethylene polyoxypropylene glyceryl ether (3BO) (8EO) (5PO) (WILBRIDE S-753, manufactured by NOF CORPORATION) | | | | | 0.45 | | |
| | 1,3-Butylene glycol | 16.20 | 16.13 | 12.00 | 16.05 | 16.05 | 16.05 | 10 |
| | Glycerin | 23.73 | 23.62 | 24.00 | 23.5 | 23.5 | 14.4 | 27.55 |
| | Sorbitol | | | | | | 13 | |
| F | Water | 23.25 | 23.25 | 23.25 | 23.25 | 23.25 | 19.35 | 23.25 |
| | Fragrance | 0.25 | 0.25 | 0.25 | 0.25 | 0.25 | 0.25 | 0.25 |
| | Total | 100.00 | 100.00 | 100.00 | 100.00 | 100.00 | 100.00 | 100.00 |
| | Content of B/% | 3.8 | 3.8 | 3.8 | 3.8 | 3.8 | 3.8 | 5.8 |
| | Content of C/% (active ingredient content) | 3.0 | 3.0 | 3.0 | 3.0 | 3.0 | 3.0 | 3.0 |
| | Content of E/% | 40.00 | 40.00 | 40.00 | 40.00 | 40.00 | 43.90 | 38.00 |
| | Content of F/% | 27.75 | 27.75 | 27.75 | 27.75 | 27.75 | 23.85 | 27.75 |
| | Content of G/% | 14.40 | 14.40 | 14.00 | 14.40 | 14.40 | 14.40 | 14.40 |
| | Total amount of (A + B)/% | 10.00 | 10.00 | 10.00 | 10.00 | 10.00 | 10.00 | 12.00 |
| | Total amount of (C + D + G)/% | 22.00 | 22.00 | 22.00 | 22.00 | 22.00 | 22.00 | 22.00 |
| | A/B | 1.61 | 1.61 | 1.61 | 1.61 | 1.61 | 1.61 | 1.06 |
| | A/D | 1.34 | 1.23 | 1.23 | 1.34 | 1.34 | 1.34 | 1.34 |
| | (A + B)/(C + D + G) | 0.45 | 0.45 | 0.45 | 0.45 | 0.45 | 0.45 | 0.55 |
| | Appearance | I | I | I | I | I | I | I |
| | Feeling that fingers stop on the skin on rinsing | 25 | 25 | 25 | 25 | 25 | 25 | 24 |
| | Absence of remaining feeling | 25 | 25 | 25 | 25 | 25 | 25 | 25 |
| | Foam retention on washing the face after makeup is removed (strokes) | 100 or more | 100 or more | 100 or more | 100 or more | 100 or more | 100 or more | 100 or more |
| | Spreadability on application | 21 | 25 | 23 | 23 | 25 | 25 | 24 |

TABLE 4-continued

| Components (% by mass) | Ex. 14 | Ex. 15 | Ex. 16 | Ex. 17 | Ex. 18 | Ex. 19 | Ex. 20 |
|---|---|---|---|---|---|---|---|
| Cleansing rate (%) | 90 | 90 | 90 | 90 | 90 | 90 | 90 |
| Moist feeling 20 minutes after cleansing | 23 | 25 | 25 | 25 | 24 | 23 | 23 |

TABLE 5

| | Components (% by mass) | Example 5 | Example 21 | Example 22 | Example 23 |
|---|---|---|---|---|---|
| A | Liquid paraffin (Viscosity: 115 mPa · s, HICALL K-350, manufactured by KANEDA Co., Ltd.) | 4.32 | 4.32 | | |
| | Liquid paraffin (Viscosity: 86 mPa · s) | | | 6.17 | |
| | Liquid paraffin (Viscosity: 198 mPa · s) | | | | 6.17 |
| B | Isononyl isononanoate (Viscosity: 7.4 mPa · s, SALACOS 99, manufactured by Nisshin Oil Mills, Ltd.) | 2.68 | 2.68 | 3.83 | 3.83 |
| C | Decyl polyglucoside (HLB 17, MYDOL 10, active ingredient content 40%, manufactured by Kao Corporation) | 7.50 | 7.50 | 7.50 | 7.50 |
| D | Diglycerin monoisostearate (HLB 8, Cosmol 41V, manufactured by The Nisshin OilliO Group, Ltd.) | 4.60 | 4.60 | 4.60 | 7.00 |
| G | Tetraoleic acid polyoxyethylene (30) sorbit (HLB 10.5, RHEODOL 430V, manufactured by Kao Corporation) | 3.00 | 3.00 | 3.00 | 3.00 |
| | Polyoxyethylene (12) monolaurate ester (HLB 13.7, EMANON 1112, manufactured by Kao Corporation) | 11.40 | 11.40 | 11.40 | 9.00 |
| E | Polyoxypropylene (9) diglyceryl ether (SY-DP9, manufactured by SAKAMOTO YAKUHIN KOGYO CO., LTD.) | 0.45 | 0 | 0.45 | 0.45 |
| | 1,3-Butylene glycol | 17.27 | 17.27 | 16.05 | 16.05 |
| | Glycerin | 25.28 | 25.28 | 23.50 | 23.50 |
| | Sorbitol | | | | |
| F | Water | 23.25 | 23.7 | 23.25 | 23.25 |
| | Fragrance | 0.25 | 0.25 | 0.25 | 0.25 |
| | Total | 100.00 | 100.00 | 100.00 | 100.00 |
| | Content of B/% | 2.7 | 2.7 | 3.8 | 3.8 |
| | Content of C/% (active ingredient content) | 3.0 | 3.0 | 3.0 | 3.0 |
| | Content of E/% | 43.00 | 42.55 | 40.00 | 40.00 |
| | Content of F/% | 27.75 | 28.20 | 27.75 | 27.75 |
| | Content of G/% | 14.40 | 14.40 | 14.40 | 12.00 |
| | Total amount of (A + B)/% | 7.00 | 7.00 | 10.00 | 10.00 |
| | Total amount of (C + D + G)/% | 22.00 | 22.00 | 22.00 | 22.00 |
| | A/B | 1.61 | 1.61 | 1.61 | 1.61 |
| | A/D | 0.94 | 0.94 | 1.34 | 0.88 |
| | (A + B)/(C + D + G) | 0.32 | 0.32 | 0.45 | 0.45 |
| | Appearance | I | I | I | I |
| | Feeling that fingers stop on the skin on rinsing | 25 | 23 | 25 | 25 |
| | Absence of remaining feeling | 25 | 24 | 25 | 25 |
| | Foam retention on washing the face after makeup is removed (strokes) | 100 or more | 80 | 100 or more | 100 or more |
| | Spreadability on application | 25 | 25 | 25 | 25 |
| | Cleansing rate (%) | 90 | 90 | 90 | 90 |
| | Moist feeling 20 minutes after cleansing | 25 | 25 | 25 | 25 |

Test Example 1

The skin cleansing compositions of Examples 2 and 8 were measured for viscosity after storage for one hour at 25° C. after production with a B-type viscometer (rotor No. 2, 30 rpm).

The results were 90 mPa·s for Example 2 and 120 mPa·s for Example 8.

Examples 24 to 49 and Comparative Examples 7 to 11

Skin cleansing compositions having the composition shown in Table 6 to Table 9 were produced, and evaluated for an appearance, spreadability one minute after application, a feeling that fingers stop on the skin on rinsing, absence of a remaining feeling, foam retention on washing the face after makeup is removed, a cleansing rate, and a moist feeling until 20 minutes after cleansing. The results are also shown in Table 6 to Table 9.

(Production Method)

All the components were placed in a vessel, stirred and mixed until homogeneous to thereby obtain the skin cleansing composition. When there was a component which is solid at 25° C., or when a gel-like component was generated by mixing at room temperature, the mixture was heated at from 70 to 75° C. with stirring for dissolution. After the component was sufficiently dissolved, the mixture was cooled to 25° C. to thereby obtain the skin cleansing composition.

All the resulting skin cleansing compositions were transparent liquid.

(Evaluation Method)

(1) Appearance:

The appearance of each skin cleansing composition was visually observed after one hour of storage at 25° C. after production.

I: monolayer.
II: bilayer.
(2) Spreadability one minute after application:
Five expert panelists applied 0.65 mg/cm² of foundation (Sofina Primavista liquid foundation, Ocher 05 (manufactured by Kao Corporation), the same foundation was used for evaluation in the tests hereinafter) on the skin of an inner forearm to a size of 3 cm×10 cm. Two grams of each skin cleansing composition was applied thereover. The area was massaged for one minute in the direction from the elbow to the wrist with a forefinger at a rate of a reciprocation per second, and spreadability one minute after was evaluated based on the following five grades. The results were indicated by the total score of the five panelists.
5: Very easy to spread.
4: Easy to spread.
3: Slightly easy to spread.
2: Difficult to spread.
1: Clearly difficult to spread.
(3) Feeling that fingers stop on the skin on rinsing:
Five expert panelists applied 0.65 mg/cm² of the foundation on the skin of an inner forearm to a size of 3 cm×10 cm. About two grams of each skin cleansing composition was applied thereover on the forearm, and ease of wash-off on rinsing by washing off with water was evaluated based on the following five grades. The results were indicated by the total score of the five panelists.
5: Clearly feel that fingers stop.
4: Feel that fingers stop.
3: Slightly feel that fingers stop.
2: Hardly feel that fingers stop.
1: Not feel that fingers stop.
(4) Absence of remaining feeling:
Five expert panelists applied 0.65 mg/cm² of the foundation on the skin of an inner forearm to a size of 3 cm×10 cm. About two grams of each skin cleansing composition was applied thereon on the forearm and rinsed by washing off with water for 20 seconds. Then, a feeling that the agent does not remain on the skin was evaluated based on the following five grades. The results were indicated by the total score of the five panelists.
5: There is clearly no remaining feeling.
4: There is no remaining feeling.
3: There is a slight remaining feeling.
2: There is a remaining feeling.
1: There is a clearly remaining feeling.
(5) Foam retention on washing the face after makeup is removed:
Each skin cleansing composition was pipetted, 1 mL was dropped on a Teflon (registered trademark) plate (5 cm×8 cm), and applied so as to extend to a diameter of 3 cm. After two seconds, the entire Teflon (registered trademark) plate was slowly immersed in water and removed out after two seconds. The operation was repeated three times. Thereafter, the Teflon (registered trademark) plate was inclined for three seconds such that the wider side was perpendicular to the ground to remove the moisture. Subsequently, one push amount (1 g) of Biore Marshmallow Whip Rich Moisture (manufactured by Kao Corporation) was placed on the area of the aforementioned plate to which the skin cleansing composition was applied and blended by fingers at a rate of one stroke per second. The number of blending strokes until the foam were decreased and 50% of the plate surface was exposed was determined.
(6) Cleansing rate:
As an oil-based mascara (waterproof mascara), 0.002 g of Kose Sports Beauty Fasio Ultracurl Lock Mascara (long) BK001 (trade name) was evenly applied on a glass slide to a circle of a diameter of 1.2 cm and left for two hours to dryness. About 0.05 g of each skin cleansing composition was placed thereon, and the oil-based mascara was massaged with fingers 50 times at a rate of three strokes per second. Then, the slide was lightly rinsed with tap water, dried for 30 minutes, and then, the weight was determined. From the weight change, the cleansing rate was determined by the following expression.
A: Weight of the glass slide (g)
B: Weight of the glass slide after application of the oil-based mascara (g)
C: Weight of the glass slide after cleansing (g)

$$\text{Cleansing rate (\%)} = \left(1 - \frac{(C-A)}{(B-A)}\right) \times 100$$

(7) Moist feeling 20 minutes after cleansing
Five expert panelists applied 1.5 g of the foundation to the entire face. About three grams of each skin cleansing composition was applied thereover on the face and rinsed by washing off with water. A moist feeling until 20 minutes passed after the moisture was wiped off with a towel was evaluated based on the following five grades. The results were indicated by the total score of the five panelists.
5: Very moist.
4: Moist.
3: Slightly moist.
2: Not so moist.
1: Clearly not moist.

TABLE 6

| | | Components (% by mass) | Ex. 24 | Ex. 25 | Ex. 26 | Ex. 27 | Ex. 28 | Ex. 29 | Ex. 30 | Comp. Ex. 7 | Comp. Ex. 8 | Comp. Ex. 9 |
|---|---|---|---|---|---|---|---|---|---|---|---|---|
| H | h1 | Polyoxypropylene (9) diglyceryl ether (SY-DP9, manufactured by SAKAMOTO YAKUHIN KOGYO CO., LTD.) | 0.07 | 0.1 | 0.25 | 0.45 | 1.5 | 4 | 8.5 | | 0.01 | 26.40 |
| I | | Isononyl isononanoate (Viscosity: 7.4 mPa·s, SALACOS 99, manufactured by Nisshin Oil Mills, Ltd.) | 3.83 | 3.83 | 3.83 | 3.83 | 3.83 | 3.83 | 3.83 | 3.83 | 3.83 | 3.83 |
| | | Liquid paraffin (Viscosity: 115 mPa·s, HICALL K-350, manufactured by KANEDA Co., Ltd.) | 6.17 | 6.17 | 6.17 | 6.17 | 6.17 | 6.17 | 6.17 | 6.17 | 6.17 | 6.17 |
| J | j1 | Decyl polyglucoside (HLB 17, MYDOL 10, active ingredient content 40%, manufactured by Kao Corporation) | 7.50 | 7.50 | 7.50 | 7.50 | 7.50 | 7.50 | 7.50 | 7.50 | 7.50 | 7.50 |

TABLE 6-continued

| | | Components (% by mass) | Ex. 24 | Ex. 25 | Ex. 26 | Ex. 27 | Ex. 28 | Ex. 29 | Ex. 30 | Comp. Ex. 7 | Comp. Ex. 8 | Comp. Ex. 9 |
|---|---|---|---|---|---|---|---|---|---|---|---|---|
| | j2 | Diglycerin monoisostearate (HLB 8, Cosmol 41V, manufactured by The Nisshin OilliO Group, Ltd.) | 4.60 | 4.60 | 5.00 | 4.60 | 5.00 | 5.00 | 5.50 | 4.60 | 4.60 | 4.60 |
| | j3 | Tetraoleic acid polyoxyethylene (30) sorbit (HLB 10.5, RHEODOL 430V, manufactured by Kao Corporation) | 3.00 | 3.00 | 3.00 | 3.00 | 3.00 | 3.00 | 3.00 | 3.00 | 3.00 | 3.00 |
| | | Polyoxyethylene (12) monolaurate ester (HLB 13.7, EMANON 1112, manufactured by Kao Corporation) | 11.40 | 11.40 | 11.00 | 11.40 | 11.00 | 11.00 | 10.50 | 11.40 | 11.40 | 11.40 |
| L | | 1,3-Butylene glycol | 16.20 | 16.19 | 16.13 | 16.05 | 15.62 | 12.00 | 7.78 | 16.05 | 16.05 | 5.52 |
| | | Glycerin | 23.73 | 23.71 | 23.62 | 23.50 | 22.88 | 24.00 | 23.72 | 23.95 | 23.94 | 8.08 |
| K | | Water | 23.25 | 23.25 | 23.25 | 23.25 | 23.25 | 23.25 | 23.25 | 23.25 | 23.25 | 23.25 |
| | | Fragrance | 0.25 | 0.25 | 0.25 | 0.25 | 0.25 | 0.25 | 0.25 | 0.25 | 0.25 | 0.25 |
| Total | | | 100.00 | 100.00 | 100.00 | 100.00 | 100.00 | 100.00 | 100.00 | 100.00 | 100.00 | 100.00 |
| Content of H/% | | | 0.07 | 0.10 | 0.25 | 0.45 | 1.50 | 4.00 | 8.50 | 0.00 | 0.01 | 26.40 |
| Content of I/% | | | 10.0 | 10.0 | 10.0 | 10.0 | 10.0 | 10.0 | 10.0 | 10.0 | 10.0 | 10.0 |
| Content of j1/% (active ingredient content) | | | 3.0 | 3.0 | 3.0 | 3.0 | 3.0 | 3.0 | 3.0 | 3.0 | 3.0 | 3.0 |
| Content of j3/% | | | 14.40 | 14.40 | 14.00 | 14.40 | 14.00 | 14.00 | 13.50 | 14.40 | 14.40 | 14.40 |
| Content of K/% | | | 27.75 | 27.75 | 27.75 | 27.75 | 27.75 | 27.75 | 27.75 | 27.75 | 27.75 | 27.75 |
| Content of L/% | | | 39.93 | 39.90 | 39.75 | 39.55 | 38.50 | 36.00 | 31.50 | 40.00 | 39.99 | 13.60 |
| (j1 + j2 + j3)/% | | | 22.00 | 22.00 | 22.00 | 22.00 | 22.00 | 22.00 | 22.00 | 22.00 | 22.00 | 22.00 |
| H/I | | | 0.007 | 0.010 | 0.025 | 0.045 | 0.150 | 0.400 | 0.850 | 0.000 | 0.001 | 2.640 |
| H/(j1 + j2 + j3) | | | 0.003 | 0.005 | 0.011 | 0.020 | 0.068 | 0.182 | 0.386 | 0.000 | 0.000 | 1.200 |
| I/(j1 + j2 + j3) | | | 0.45 | 0.45 | 0.40 | 0.45 | 0.45 | 0.45 | 0.45 | 0.45 | 0.45 | 0.45 |
| Appearance | | | I | I | I | I | I | I | I | I | I | II |
| Spreadability one minute after application | | | 21 | 23 | 25 | 25 | 25 | 23 | 21 | 16 | 17 | 16 |
| Feeling that fingers stop on the skin on rinsing | | | 25 | 25 | 25 | 25 | 25 | 25 | 23 | 16 | 17 | 15 |
| Absence of remaining feeling | | | 25 | 25 | 25 | 25 | 25 | 25 | 23 | 17 | 18 | 15 |
| Foam retention on washing the face after makeup is removed (strokes) | | | 100 or more | 100 or more | 100 or more | 100 or more | 100 or more | 100 or more | 100 or more | 50 | 50 | 50 |
| Cleansing rate (%) | | | 90 | 90 | 90 | 90 | 90 | 90 | 90 | 90 | 90 | 80 |
| Moist feeling 20 minutes after cleansing | | | 23 | 23 | 25 | 25 | 25 | 25 | 25 | 18 | 18 | 22 |

TABLE 7

| | | Components (% by mass) | Ex. 31 | Ex. 27 | Ex. 32 | Ex. 33 | Ex. 34 | Ex. 27 | Ex. 35 |
|---|---|---|---|---|---|---|---|---|---|
| H | h1 | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 | 0.45 | 0.45 |
| I | | Isononyl isononanoate (Viscosity: 7.4 mPa · s, SALACOS 99, manufactured by Nisshin Oil Mills, Ltd.) | 1.00 | 3.83 | 9.00 | 1.92 | 2.68 | 3.83 | 6.13 |
| | | Liquid paraffin (Viscosity: 115 mPa · s, HICALL K-350, manufactured by KANEDA Co., Ltd.) | 9.00 | 6.17 | 1.00 | 3.08 | 4.32 | 6.17 | 9.87 |
| J | j1 | Decyl polyglucoside (HLB 17, MYDOL 10, active ingredient content 40%, manufactured by Kao Corporation) | 7.50 | 7.50 | 7.50 | 7.50 | 7.50 | 7.50 | 7.50 |
| | j2 | Diglycerin monoisostearate (HLB 8, Cosmol 41V, manufactured by The Nisshin OilliO Group, Ltd.) | 4.60 | 4.60 | 4.60 | 4.60 | 4.60 | 4.60 | 5.77 |
| | j3 | Tetraoleic acid polyoxyethylene (30) sorbit (HLB 10.5, RHEODOL 430V, manufactured by Kao Corporation] | 3.00 | 3.00 | 3.00 | 3.00 | 3.00 | 3.00 | 3.00 |
| | | Polyoxyethylene (12) monolaurate ester (HLB 13.7, EMANON 1112, manufactured by Kao Corporation) | 11.40 | 11.40 | 11.40 | 11.40 | 11.40 | 11.40 | 10.23 |
| L | | 1,3-Butylene glycol | 16.05 | 16.05 | 16.05 | 18.08 | 17.27 | 16.05 | 13.61 |
| | | Glycerin | 23.50 | 23.50 | 23.50 | 26.47 | 25.28 | 23.50 | 19.94 |
| K | | Water | 23.25 | 23.25 | 23.25 | 23.25 | 23.25 | 23.25 | 23.25 |
| | | Fragrance | 0.25 | 0.25 | 0.25 | 0.25 | 0.25 | 0.25 | 0.25 |
| Total | | | 100.00 | 100.00 | 100.00 | 100.00 | 100.00 | 100.00 | 100.00 |
| Content of H/% | | | 0.45 | 0.45 | 0.45 | 0.45 | 0.45 | 0.45 | 0.45 |
| Content of I/% | | | 10.0 | 10.0 | 10.0 | 5.0 | 7.0 | 10.0 | 16.0 |
| Content of j1/% (active ingredient content) | | | 3.0 | 3.0 | 3.0 | 3.0 | 3.0 | 3.0 | 3.0 |
| Content of j3/% | | | 14.40 | 14.40 | 14.40 | 14.40 | 14.40 | 14.40 | 13.23 |
| Content of K/% | | | 27.75 | 27.75 | 27.75 | 27.75 | 27.75 | 27.75 | 27.75 |
| Content of L/% | | | 39.55 | 39.55 | 39.55 | 44.55 | 42.55 | 39.55 | 33.55 |
| (j1 + j2 + j3)/% | | | 22.00 | 22.00 | 22.00 | 22.00 | 22.00 | 22.00 | 22.00 |
| H/I | | | 0.045 | 0.045 | 0.045 | 0.090 | 0.064 | 0.045 | 0.028 |

TABLE 7-continued

| | | | | | | | |
|---|---|---|---|---|---|---|---|
| H/(j1 + j2 + j3) | 0.020 | 0.020 | 0.020 | 0.020 | 0.020 | 0.020 | 0.020 |
| I/(j1 + j2 + j3) | 0.45 | 0.45 | 0.45 | 0.23 | 0.32 | 0.45 | 0.73 |
| Appearance | I | I | I | I | I | I | I |
| Spreadability one minute after application | 23 | 25 | 25 | 25 | 25 | 25 | 25 |
| Feeling that fingers stop on the skin on rinsing | 23 | 25 | 23 | 25 | 25 | 25 | 25 |
| Absence of remaining feeling | 23 | 25 | 24 | 25 | 25 | 25 | 25 |
| Foam retention on washing the face after makeup is removed (strokes) | 80 | 100 or more | 80 | 100 or more | 100 or more | 100 or more | 100 or more |
| Cleansing rate (%) | 80 | 90 | 92 | 80 | 90 | 90 | 90 |
| Moist feeling 20 minutes after cleansing | 25 | 25 | 23 | 25 | 25 | 25 | 25 |

| | | | Components (% by mass) | Ex. 36 | Ex. 37 | Ex. 38 | Ex. 27 | Ex. 39 | Ex. 40 |
|---|---|---|---|---|---|---|---|---|---|
| H | h1 | | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 | 0.45 |
| I | | | Isononyl isononanoate (Viscosity: 7.4 mPa · s, SALACOS 99, manufactured by Nisshin Oil Mills, Ltd.) | 11.49 | 3.83 | 3.83 | 3.83 | 3.83 | 3.83 |
| | | | Liquid paraffin (Viscosity: 115 mPa · s, HICALL K-350, manufactured by KANEDA Co., Ltd.) | 18.51 | 6.17 | 6.17 | 6.17 | 6.17 | 6.17 |
| J | j1 | | Decyl polyglucoside (HLB 17, MYDOL 10, active ingredient content 40%, manufactured by Kao Corporation) | 7.50 | 2.73 | 5.45 | 7.50 | 9.55 | 15.68 |
| | j2 | | Diglycerin monoisostearate (HLB 8, Cosmol 41V, manufactured by The Nisshin OilliO Group, Ltd.) | 8.50 | 2.70 | 3.35 | 4.60 | 5.85 | 9.62 |
| | j3 | | Tetraoleic acid polyoxyethylene (30) sorbit (HLB 10.5, RHEODOL 430V, manufactured by Kao Corporation) | 3.00 | 1.09 | 2.18 | 3.00 | 3.82 | 6.27 |
| | | | Polyoxyethylene (12) monolaurate ester (HLB 13.7, EMANON 1112, manufactured by Kao Corporation) | 7.50 | 3.12 | 8.29 | 11.40 | 14.51 | 23.84 |
| L | | | 1,3-Butylene glycol | 7.9 | 18 | 18.48 | 16.05 | 13.62 | 6.31 |
| | | | Glycerin | 11.65 | 27 | 27.07 | 23.50 | 19.93 | 9.24 |
| K | | | Water | 23.25 | 34.66 | 24.48 | 23.25 | 22.02 | 18.34 |
| | | | Fragrance | 0.25 | 0.25 | 0.25 | 0.25 | 0.25 | 0.25 |
| | | | Total | 100.00 | 100.00 | 100.00 | 100.00 | 100.00 | 100.00 |
| | | | Content of H/% | 0.45 | 0.45 | 0.45 | 0.45 | 0.45 | 0.45 |
| | | | Content of I/% | 30.0 | 10.0 | 10.0 | 10.0 | 10.0 | 10.0 |
| | | | Content of j1/% (active ingredient content) | 3.0 | 1.1 | 2.2 | 3.0 | 3.8 | 6.3 |
| | | | Content of j3/% | 10.50 | 4.21 | 10.47 | 14.40 | 18.33 | 30.11 |
| | | | Content of K/% | 27.75 | 36.30 | 27.75 | 27.75 | 27.75 | 27.75 |
| | | | Content of L/% | 19.55 | 45.00 | 45.55 | 39.55 | 33.55 | 15.55 |
| | | | (j1 + j2 + j3)/% | 22.00 | 8.00 | 16.00 | 22.00 | 28.00 | 46.00 |
| | | | H/I | 0.015 | 0.045 | 0.045 | 0.045 | 0.045 | 0.045 |
| | | | H/(j1 + j2 + j3) | 0.020 | 0.056 | 0.028 | 0.020 | 0.016 | 0.010 |
| | | | I/(j1 + j2 + j3) | 1.36 | 1.25 | 0.63 | 0.45 | 0.36 | 0.22 |
| | | | Appearance | I | I | I | I | I | I |
| | | | Spreadability one minute after application | 23 | 25 | 25 | 25 | 25 | 23 |
| | | | Feeling that fingers stop on the skin on rinsing | 22 | 23 | 25 | 25 | 25 | 25 |
| | | | Absence of remaining feeling | 22 | 23 | 25 | 25 | 25 | 23 |
| | | | Foam retention on washing the face after makeup is removed (strokes) | 80 | 82 | 100 or more | 100 or more | 100 or more | 100 or more |
| | | | Cleansing rate (%) | | 95 | 90 | 90 | 90 | 85 |
| | | | Moist feeling 20 minutes after cleansing | 23 | 25 | 25 | 25 | 25 | 25 |

TABLE 8

| | | Components (% by mass) | Example 41 | Example 27 | Example 42 | Comp. Ex. 10 | Comp. Ex. 11 |
|---|---|---|---|---|---|---|---|
| H | h1 | Polyoxypropylene (9) diglyceryl ether (SY-DP9, manufactured by SAKAMOTO YAKUHIN KOGYO CO., LTD.) | 0.45 | 0.45 | 0.45 | 0.45 | 0.45 |
| I | | Isononyl isononanoate (Viscosity: 7.4 mPa · s, SALACOS 99, manufactured by Nisshin Oil Mills, Ltd.) | 3.83 | 3.83 | 3.83 | 3.83 | 3.83 |
| | | Liquid paraffin (Viscosity: 115 mPa · s, HICALL K-350, manufactured by KANEDA Co., Ltd.) | 6.17 | 6.17 | 6.17 | 6.17 | 6.17 |
| J | j1 | Decyl polyglucoside (HLB 17, MYDOL 10, active ingredient content 40%, manufactured by Kao Corporation) | 7.50 | 7.50 | 7.50 | 7.50 | 7.50 |

TABLE 8-continued

| | Components (% by mass) | Example 41 | Example 27 | Example 42 | Comp. Ex. 10 | Comp. Ex. 11 |
|---|---|---|---|---|---|---|
| | j2 Diglycerin monoisostearate (HLB 8, Cosmol 41V, manufactured by The Nisshin OilliO Group, Ltd.) | 4.60 | 4.60 | 4.60 | 4.60 | 4.60 |
| | j3 Tetraoleic acid polyoxyethylene (30) sorbit (HLB 10.5, RHEODOL 430V, manufactured by Kao Corporation) | 3.00 | 3.00 | 3.00 | 3.00 | 3.00 |
| | Polyoxyethylene (12) monolaurate ester (HLB 13.7, EMANON 1112, manufactured by Kao Corporation) | 11.40 | 11.40 | 11.40 | 11.40 | 11.40 |
| L | 1,3-Butylene glycol | 20.21 | 16.05 | 7.22 | 24.28 | 3.77 |
| | Glycerin | 29.59 | 23.50 | 10.58 | 35.52 | 5.53 |
| K | Water | 13 | 23.25 | 45 | 3.00 | 53.50 |
| | Fragrance | 0.25 | 0.25 | 0.25 | 0.25 | 0.25 |
| Total | | 100.00 | 100.00 | 100.00 | 100.00 | 100.00 |
| Content of H/% | | 0.45 | 0.45 | 0.45 | 0.45 | 0.45 |
| Content of I/% | | 10.0 | 10.0 | 10.0 | 10.0 | 10.0 |
| Content of j1/% (active ingredient content) | | 3.0 | 3.0 | 3.0 | 3.0 | 3.0 |
| Content of j3/% | | 14.40 | 14.40 | 14.40 | 14.40 | 14.40 |
| Content of K/% | | 17.50 | 27.75 | 49.50 | 7.50 | 58.00 |
| Content of L/% | | 49.80 | 39.55 | 17.80 | 59.80 | 9.30 |
| (j1 + j2 + j3)/% | | 22.00 | 22.00 | 22.00 | 22.00 | 22.00 |
| H/I | | 0.045 | 0.045 | 0.045 | 0.045 | 0.045 |
| H/(j1 + j2 + j3) | | 0.020 | 0.020 | 0.020 | 0.020 | 0.020 |
| I/(j1 + j2 + j3) | | 0.45 | 0.45 | 0.45 | 0.45 | 0.45 |
| Appearance | | I | I | I | II | I |
| Spreadability one minute after application | | 23 | 25 | 25 | 16 | 22 |
| Feeling that fingers stop on the skin on rinsing | | 25 | 25 | 25 | 18 | 22 |
| Absence of remaining feeling | | 25 | 25 | 25 | 17 | 22 |
| Foam retention on washing the face after makeup is removed (strokes) | | 100 or more | 100 or more | 100 or more | 90 | 90 |
| Cleansing rate (%) | | 90 | 90 | 85 | 50 | 50 |
| Moist feeling 20 minutes after cleansing | | 25 | 25 | 23 | 18 | 18 |

TABLE 9

| | | Components (% by mass) | Ex. 43 | Ex. 44 | Ex. 45 | Ex. 46 | Ex. 47 | Ex. 48 | Ex. 49 |
|---|---|---|---|---|---|---|---|---|---|
| H | h1 | Polyoxypropylene (9) diglyceryl ether (SY-DP9, manufactured by SAKAMOTO YAKUHIN KOGYO CO., LTD.) | | | 0.45 | 0.45 | 0.45 | 0.45 | 8.00 |
| | | Polyoxypropylene (14) diglyceryl ether (SY-DP14, manufactured by SAKAMOTO YAKUHIN KOGYO CO., LTD.) | 0.45 | | | | | | |
| | h2 | Polyoxybutylene polyoxyethylene polyoxypropylene glyceryl ether (3BO) (8EO) (5PO) (WILBRIDE S-753, manufactured by NOF CORPORATION) | | 0.45 | | | | | |
| I | | Isononyl isononanoate (Viscosity: 7.4 mPa·s, SALACOS 99, manufactured by Nisshin Oil Mills, Ltd.) | 3.83 | 3.83 | 3.83 | | 3.83 | | 4.98 |
| | | Tri(caprylic/capric acid)glyceryl (Viscosity 27 mPa·s, COCONARD MT, manufactured by Kao Corporation) | | | | | 1.00 | | |
| | | Light liquid isoparaffin (Viscosity: 5 mPa·s, MARUKASOL R, manufactured by Maruzen Petrochemical Co., Ltd.) | | | | 6.17 | | 10.00 | |
| | | Dicaprylyl ether (Viscosity: 5 mPa·s, Cetiol OE, manufactured by Cognis Corporation) | | | | 3.83 | | | |
| | | Decamethylcyclopentasiloxane: 3 mPa·s (Silicone SH245, manufactured by Dow Corning Toray Co., Ltd.) | | | | | 1.00 | | |
| | | Liquid paraffin (Viscosity: 115 mPa·s, HICALL K-350, manufactured by KANEDA Co., Ltd.) | 6.17 | 6.17 | 6.17 | | 6.17 | | 8.02 |
| J | j1 | Decyl polyglucoside (HLB 17, MYDOL 10, active ingredient content 40%, manufactured by Kao Corporation) | 7.50 | 7.50 | 7.50 | 7.50 | 7.50 | 7.50 | 13.6 |
| | j2 | Diglycerin monoisostearate (HLB 8, Cosmol 41V, manufactured by The Nisshin OilliO Group, Ltd.) | 4.60 | 4.60 | 4.60 | 4.60 | 4.60 | 4.60 | 8.32 |

TABLE 9-continued

| Components (% by mass) | | Ex. 43 | Ex. 44 | Ex. 45 | Ex. 46 | Ex. 47 | Ex. 48 | Ex. 49 |
|---|---|---|---|---|---|---|---|---|
| | j3 Tetraoleic acid polyoxyethylene (30) sorbit (HLB 10.5, RHEODOL 430V, manufactured by Kao Corporation) | 3.00 | 3.00 | 3.00 | 3.00 | 3.00 | 3.00 | 5.44 |
| | Polyoxyethylene (12) monolaurate ester (HLB 13.7, EMANON 1112, manufactured by Kao Corporation) | 11.40 | 11.40 | 11.40 | 11.40 | 11.40 | 11.40 | 20.8 |
| L | 1,3-Butylene glycol | 16.05 | 16.05 | 16.05 | 16.05 | 10 | 16.05 | |
| | Glycerin | 23.5 | 23.5 | 14.4 | 23.5 | 27.55 | 23.50 | |
| | Sorbitol | | | 13 | | | | |
| K | Water | 23.25 | 23.25 | 19.35 | 23.25 | 23.25 | 23.25 | 30.59 |
| | Fragrance | 0.25 | 0.25 | 0.25 | 0.25 | 0.25 | 0.25 | 0.25 |
| Total | | 100.00 | 100.00 | 100.00 | 100.00 | 100.00 | 100.00 | 100.00 |
| Content of H/% | | 0.45 | 0.45 | 0.45 | 0.45 | 0.45 | 0.45 | 8.00 |
| Content of I/% | | 10.0 | 10.0 | 10.0 | 10.0 | 12.0 | 10.0 | 13.0 |
| Content of j1/% (active ingredient content) | | 3.0 | 3.0 | 3.0 | 3.0 | 3.0 | 3.0 | 5.4 |
| Content of j3/% | | 14.40 | 14.40 | 14.40 | 14.40 | 14.40 | 14.40 | 26.24 |
| Content of K/% | | 27.75 | 27.75 | 23.85 | 27.75 | 27.75 | 27.75 | 38.75 |
| Content of L/% | | 39.55 | 39.55 | 43.45 | 39.55 | 37.55 | 39.55 | 0.00 |
| (j1 + j2 + j3)/% | | 22.00 | 22.00 | 22.00 | 22.00 | 22.00 | 22.00 | 40.00 |
| H/I | | 0.045 | 0.045 | 0.045 | 0.045 | 0.038 | 0.045 | 0.615 |
| H/(j1 + j2 + j3) | | 0.020 | 0.020 | 0.020 | 0.020 | 0.020 | 0.020 | 0.200 |
| I/(j1 + j2 + j3) | | 0.45 | 0.45 | 0.45 | 0.45 | 0.55 | 0.45 | 0.33 |
| Appearance | | I | I | I | I | I | I | I |
| Spreadability one minute after application | | 23 | 25 | 25 | 25 | 24 | 25 | 20 |
| Feeling that fingers stop on the skin on rinsing | | 25 | 25 | 25 | 25 | 24 | 25 | 22 |
| Absence of remaining feeling | | 25 | 25 | 25 | 25 | 25 | 25 | 23 |
| Foam retention on washing the face after makeup is removed (strokes) | | 100 or more | 100 or more | 100 or more | 100 or more | 100 or more | 70 | 100 or more |
| Cleansing rate (%) | | 90 | 90 | 90 | 95 | 90 | 90 | 90 |
| Moist feeling 20 minutes after cleansing | | 25 | 24 | 23 | 24 | 25 | 23 | 23 |

Test Example 2

The skin cleansing compositions of Examples 27 and 40 were measured for viscosity after storage for one hour at 25° C. after production with a B-type viscometer (rotor No. 2, 30 rpm).

The results were 90 mPa·s for Example 27 and 130 mPa·s for Example 40.

The invention claimed is:

1. A skin cleansing composition comprising the following components (H), (I), (J), and (K):
(H) from 0.05 to 10% by mass of one or more glycerin derivatives selected from the group consisting of (h1) and (h2):

(h1) the formula (1)

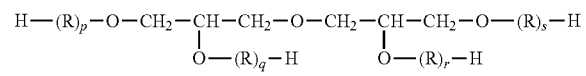

wherein R represents —[CH$_2$CH(CH$_3$)O]—, p, q, r, and s each represent an integer of from 0 to 20, and p+q+r+s represents an integer of from 4 to 20, (h2) the formula (2)

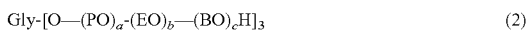

wherein Gly represents a residue obtained by removing hydroxyl groups from glycerin, PO represents an oxypropylene group, EO represents an oxyethylene group, a and b are the average addition mole number of each PO and DO and represent a value of from 1 to 50, the mass ratio of PO to EO, PO/EO, is from 1/5 to 5/1, BO represents an oxyalkylene group having 4 carbon atoms, and c is the average addition mole number of BO and represents a value of from 1 to 5, (I) from 3 to 35% by mass of an oil agent which is liquid at 30° C., (J) from 5 to 50% by mass of a nonionic surfactant selected from the group consisting of (j1), (j2), and (j3) and comprising at least (j1) and (j2), (j1) a nonionic surfactant having an HLB of 10 or more and having a residue obtained by removing a hydrogen atom from at least one hydroxyl group in sugar, reducing sugar, or polyglycerin as a hydrophilic group, (j2) a nonionic surfactant having an HLB of 8 or less, and (j3) a nonionic surfactant having an HLB of 10 or more and having a polyoxyethylene chain as a hydrophilic group, and (K) from 10 to 50% by mass of water, wherein the mass ratio of the component (H) to (J), ((H)/(J)), is from 0.001 to 0.5, wherein said composition comprises an isotropic single liquid phase exhibiting a bicontinuous structure.

2. The skin cleansing composition according to claim 1, wherein the mass ratio of the component (H) to the component (I), ((H)/(I)), is from 0.001 to 1.

3. The skin cleansing composition according to claim 1, wherein the mass ratio of the component (I) to the component (J), ((I)/(J)), is from 0.1 to 1.5.

4. The skin cleansing composition according to claim 1, further comprising from 10 to 60% by mass of (L) a polyhydric alcohol other than the component (H).

5. The skin cleansing composition according to claim 1, wherein the content of the component (H) is 0.07% by mass or more and 8.5% by mass or less in the whole composition.

6. The skin cleansing composition according to claim 1, wherein the component (I) has a viscosity at 30° C. of from 1 to 1,000 mPa·s.

7. The skin cleansing composition according to claim 1, wherein the component (I) oil agent used is a combination of an oil agent having a viscosity at 30° C. of 30 mPa·s or less and an oil agent having a viscosity at 30° C. of more than 30 mPa·s.

8. The skin cleansing composition according to claim 1, wherein the content of the component (I) is 4% by mass or more and 25% by mass or less in the whole composition.

9. The skin cleansing composition according to claim 1, wherein the component (j1) nonionic surfactant is a polyglycerin fatty acid ester, a polyglycerin alkyl ether, a sucrose fatty acid ester, and an alkyl polyglucoside.

10. The skin cleansing composition according to claim 1, wherein the component (j2) nonionic surfactant is at least one selected from the group consisting of a monoglycerin monofatty acid ester, a polyglycerin monofatty acid ester, and a monoglycerin monoalkyl ether.

11. The skin cleansing composition according to claim 1, wherein the component (j3) nonionic surfactant is at least one selected from the group consisting of a polyoxyethylene monofatty acid ester, a polyoxyethylene glycerin fatty acid ester, a tetrafatty acid polyoxyethylene sorbit, and polyoxyethylene sorbitan fatty acid ester.

12. The skin cleansing composition according to claim 1, wherein the total mass of the components (j1), (j2), and (j3) is 8% by mass or more, and 46% by mass or less in the whole composition.

13. The skin cleansing composition according to claim 1, wherein the content of the component (K) is 17% by mass or more and 45% by mass or less in the whole composition.

14. The skin cleansing composition according to claim 4, wherein the component (L) polyhydric alcohol is at least one selected from the group consisting of 1,3-butylene glycol, propylene glycol, glycerin, sorbitol, diglycerin, dipropylene glycol, 1,3-propanediol, polyoxyethylene methyl glucoside, and polyethylene glycols having a number average molecular weight of 2,000 or less.

15. The skin cleansing composition according to claim 4, wherein the component (L) polyhydric alcohol is at least one selected from the group consisting of 1,3-butylene glycol, glycerin, or sorbitol.

16. The skin cleansing composition according to claim 4, wherein the content of the component (L) is 15.5% by mass or more and 45.6% by mass or less in the whole composition.

17. The skin cleansing composition according to claim 1, wherein the composition is transparent liquid.

* * * * *